(12) United States Patent
Wallin

(10) Patent No.: US 8,647,868 B2
(45) Date of Patent: Feb. 11, 2014

(54) COMPOSITIONS AND METHODS FOR INCREASING PRODUCTION OF RECOMBINANT GAMMA-CARBOXYLATED PROTEINS

(75) Inventor: Reidar Wallin, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 935 days.

(21) Appl. No.: 12/095,514

(22) PCT Filed: Dec. 4, 2006

(86) PCT No.: PCT/US2006/061575
§ 371 (c)(1),
(2), (4) Date: Sep. 7, 2010

(87) PCT Pub. No.: WO2007/065173
PCT Pub. Date: Jun. 7, 2007

(65) Prior Publication Data
US 2010/0331255 A1 Dec. 30, 2010

Related U.S. Application Data

(60) Provisional application No. 60/742,076, filed on Dec. 2, 2005, provisional application No. 60/782,056, filed on Mar. 14, 2006.

(51) Int. Cl.
*C12N 5/00* (2006.01)
*C12P 21/06* (2006.01)
*C12N 15/00* (2006.01)
*A61K 38/36* (2006.01)
*C07H 21/02* (2006.01)

(52) U.S. Cl.
USPC ....... 435/325; 435/69.6; 435/320.1; 530/384; 536/24.5

(58) Field of Classification Search
None
See application file for complete search history.

(56) References Cited

U.S. PATENT DOCUMENTS

| | | | |
|---|---|---|---|
| 2004/0023356 A1* | 2/2004 | Krumlauf et al. | 435/226 |
| 2006/0073117 A1* | 4/2006 | Li | 424/93.1 |
| 2006/0194284 A1* | 8/2006 | Scheiflinger et al. | 435/69.1 |
| 2008/0064038 A1* | 3/2008 | Fryns et al. | 435/6 |
| 2008/0226681 A1* | 9/2008 | Goletz et al. | 424/278.1 |

FOREIGN PATENT DOCUMENTS

| | | |
|---|---|---|
| WO | 2006/067116 | 6/2006 |
| WO | 2006/110083 | 10/2006 |

OTHER PUBLICATIONS

Wajih et al (J. Biol. Chem. 279(24: 25276-25283, 2004).*
Wajih, N., et al. "Increased Production of Function Recombinant Human Clotting Factor IX by Baby Hamster Kidney Cells Engineered to Overexpress VKORC1, the Vitamin K 2,3-Epoxide-reducing Enzyme of the Vitamin K Cycle." Journal of Biological Chemistry, 280(36): 31603-31607 (Sep. 9, 2005).
Wajih, N., et al. "Engineering of a Recombinant Vitamin K-dependent γ-Carboxylation System with Enhanced γCarboxyglutamic Acid Forming Capacity." Journal of Biological Chemistry, 208(11): 10540-10547 (Mar. 18, 2005).
Wajih, N., et al. "siRNA silencing of calumenin enhances functional factor IX production." Blood, 108(12): 3757-3760 (Aug. 10, 2006).
Sun, Y., et al. "Vitamin K epoxide reductase significantly improves carboxylation in a cell line overexpressing factor X." Blood, 106(12): 3811-3815 (Dec. 1, 2005).
Wajih, N., et al. Genbank Accession DQ013267.1. Hamster calumenin cDNA sequence from lung (May 16, 2005).
Wajih, N., et al. "The inhibitory effect of calurnenin on the vitamin K-dependent gamma-carboxylation system—Characterization of the system in normal and warfarin-resistant rats." Journal of Biological Chemistry, 279(24): 25276-25283 (Jun. 11, 2004).
Wallin, R., et al. "A molecular mechanism for genetic warfarin resistance in the rat." Fed. of American Soc. for Experimental Biology Journal, 15: 2542-2544 (Sep. 17, 2001).
Roth, D., et al. "Human recombinant factor IX: Safety and efficacy studies in hemophilia B patients previously treated with plasma-derived factor IX concentrates." Blood, 98(13): 3600-3606 (Dec. 15, 2001).
Kaufman, R. J., et al. "Expression purification and characterization of recombinant gamma carboxylated factor-IX synthesized in Chinese hamster ovary cells." Journal of Biological Chemistry, 261(21): 9622-9628 (Jul. 25, 1986).

* cited by examiner

*Primary Examiner* — Richard Schnizer
(74) *Attorney, Agent, or Firm* — Dann, Dorfman, Herrell & Skillman; Kathleen D. Rigaut

(57) ABSTRACT

Methods and cell lines for overexpressing functional gamma-carboxylated proteins are disclosed by way of genetically engineered cell lines which over-express VKORC1. Also disclosed is the antisense inhibition of expression of calumenin in conjunction with overexpression of VKORC1 which also increases expression of functional gamma-carboxylated proteins. Gamma-carboxylated proteins of interest may include blood coagulation factors such as human clotting factors IX and VII.

4 Claims, 14 Drawing Sheets

Figure 8A

MDLRQFLLCLSLCTAFALSKPTEKKDRVHHEPQLSDKVHNDAQN

FDYDHDAFLGAEEAKSFDQLTPEESKERLGKIVSKIDDDKDGFVTVDELKGWIKFAQK

RWIHEDVERQWKGHDLNEDGLVSWEEYKNATYGYVLDDPDPDDGFNYKQMMVRDERRF

KMADKDGDLIATKEEFTAFPHPDEYDYMKDIVVQETMEDIDKNADGFIDLEEYIGDMY

SHDGNADEPEWVKTEREQFVEFRDKNRDGRMDKEETKDWILPSDYDHAEAEARHLVYE

SDQNKDGKLTKEEIVDKYDLFVGSQATDFGEALVRHDEF"

Figure 8B

```
  1 atggacctgcgtcagtttcttctgtgcctgtccctgtgtacagcctttgcactgagcaag
 61 cctactgaaaaaaaggaccgagtacaccatgaacctcagctcagcgacaaagttcacaac
121 gatgctcagaattttgactatgaccatgatgccttcttgggtgcagaagaagcaaagagt
181 tttgatcagctgacaccagaagagagcaaggaaaggcttggaaagattgtaagtaaaata
241 gatgacgacaaggatgggtttgtcactgtggatgaactcaaaggctggattaagtttgca
301 caaaagcgctggattcacgaggatgtagagcggcaatggaaggggcacgacctcaatgag
361 gatggcctcgtttcctgggaggagtataaaaatgccacctacggctacgttttagatgat
421 ccagaccctgatgatggattcaattataaacagatgatggttagagatgagcggaggttt
481 aaaatggcagacaaggatggagacctgattgccacaaaggaggaatttaccgctttcccg
541 caccctgatgagtatgactacatgaaagacatagttgtgcaggaaacaatggaggatata
601 gacaagaatgctgatggtttcattgatctagaagagtatattggtgacatgtacagtcat
661 gatgggaacgctgatgagccagagtgggtgaagacagagcgagaacagtttgttgagttt
721 cgagataagaaccgggatggaggatggacaaggaggagaccaaagactggatcctcct
781 tccgactatgaccacgcagaggccgaggccaggcatctagtctacgagtcagaccaaaac
841 aaggatggcaagcttaccaaggaggagattgtcgacaagtatgatttatttgtgggcagc
901 caggccacagattttggggaggccttagtgcgacacgatgagttctaagctgcaa
```

Ensembl Exon Report

| | |
|---|---|
| Transcript | CALU (HGNC Symbol ID) (to view all Ensembl genes linked to the name click here) This transcript is a member of the human CCDS set: CCDS5805 |
| Ensembl Transcript ID | ENST00000249364 |
| Transcript information | Exons: 7 Transcript length: 3,316 bps Translation length: 315 residues This transcript is a product of gene: ENSG00000128595 |
| Genomic Location | This transcript can be found on Chromosome 7 at location 127,973,387-128,005,478. The start of this transcript is located in Contig AC024952.4.1.182429. |
| Description | Calumenin precursor (Crocalbin) (IEF SSP 9302) Source: Uniprot/SWISSPROT O43852. |
| Rendering options | Flanking sequence at either end of transcript [50] Intron base pairs to show at splice sites [25] Show full intronic sequence [ ] Show exons only [ ] [Go] |

Figure 9

Exon Information

| No | Exon / Intron | Chr | Strand | Start | End | Start Phase | End Phase | Length | Sequence | SEQ ID NO: |
|---|---|---|---|---|---|---|---|---|---|---|
| | 5' upstream sequence | | | | | | | | ......gtgcggaccgcttccggttgggc ggtgctgcgcgcgtgagctgagccg | 17 |
| 1 | ENSE00001208327 | 7 | 1 | 127,973,387 | 127,973,437 | - | - | 51 | GTGCGTAGCGCGGCCGGCCACGCATCCTGTGCTGT GGGCCTACAAGGAAAG | 18 |
| | Intron 1-2 | 7 | 1 | 127,973,438 | 127,982,577 | | | 9,140 | gtaagtacggtgatgccagccct........ ..ttaactg ctttcattcattcttcaag | 19 |
| 2 | ENSE00012877 09 | 7 | 1 | 127,982,578 | 127,982,809 | - | 2 | 232 | ATCTATTATCATGGACCTGGACAGTTTCTTAT CTGCCTGTCCTGTGACCTGAAGGACCCTTGCCTGACC AAACCCACAGAAAGAAGGACGACCGTGTACATCAT AGCCTCAGTCAGTGACAAGTTCACAATGATGC TCAGAGTTTTGATTATGACCATGATGCCTTCTG GGTGCTGAAGAAGCAAAGACCTTTGATCAGCTGA CACCAGAGAG AGCAAGGAAGACTTTG | 20, 21 |
| | Intron 2-3 | 7 | 1 | 127,982,810 | 127,988,266 | | | 5,457 | gtaagctaccacctctcagggtct........ .ctggattctctgctcattctctaag | 22, 23 |
| 3 | ENSE00008820 81 | 7 | 1 | 127,988,267 | 127,988,460 | 2 | 1 | 194 | AAAGATTGTAATAAAATAGATGCCACAAGGAC GGCTTGTCACTGTGGATGAGCTCAA AGACTGGATTAAATTGCACAAAGGCGTGGATT TAGAGAGTAGAGCCGCAGTGGAA CCGGCATCACCTCCAATCAGACAGCTCCTTCC TGGCAGAGTATATAAAAATGCCACCTA CGGCTCACGTTTTAG | 24 |
| | Intron 3-4 | 7 | 1 | 127,988,461 | 127,992,875 | | | 4,415 | gtaggtcctactgtctcggggaaa........ .tttcacctaaattttctgttttctaag | 25, 26 |
| 4 | ENSE00008820 83 | 7 | 1 | 127,992,876 | 127,993,042 | 1 | 0 | 167 | ATGATCCAGATCCTGATGATTGGATTTAACTATAA ACACATGCATGGTTAGAGATGCAGCCCACGTTTAAA ATGCCAGACAAGCATGTGAGACCTCATTGCCACCA AGGAGGAGTTCCACACTTTCCTGCCACCCTGARGA GTATCACTACATGCAAGAATATAGTAGTACAG | 27 |
| | Intron 4-5 | 7 | 1 | 127,993,043 | 127,993,796 | | | 754 | gtggtcgagatgaagaattctgaac........ .tctctcctattcttcctgtttag | 28, 29 |
| 5 | ENSE00008820 | 7 | 1 | 127,993,797 | 127,993,857 | 0 | 1 | 61 | GAAAACAATGCAAGAATAAGAATGCAGATG | 30 |

SEQUENCE LISTING

<160> NUMBER OF SEQ ID NOS: 37

<210> SEQ ID NO 1
<211> LENGTH: 315
<212> TYPE: PRT
<213> ORGANISM: Hamster

<400> SEQUENCE: 1

```
Met Asp Leu Arg Gln Phe Leu Leu Cys Leu Ser Leu Cys Thr Ala Phe
 1               5                  10                  15

Ala Leu Ser Lys Pro Thr Glu Lys Lys Asp Arg Val His His Glu Pro
             20                  25                  30

Gln Leu Ser Asp Lys Val His Asn Asp Ala Gln Asn Phe Asp Tyr Asp
         35                  40                  45

His Asp Ala Phe Leu Gly Ala Glu Ala Lys Ser Phe Asp Gln Leu
     50                  55                  60

Thr Pro Glu Glu Ser Lys Glu Arg Leu Gly Lys Ile Val Ser Lys Ile
 65                  70                  75                  80

Asp Asp Asp Lys Asp Gly Phe Val Thr Val Asp Glu Leu Lys Gly Trp
                 85                  90                  95

Ile Lys Phe Ala Gln Lys Arg Trp Ile His Glu Asp Val Glu Arg Gln
                100                 105                 110

Trp Lys Gly His Asp Leu Asn Glu Asp Gly Leu Val Ser Trp Glu Glu
            115                 120                 125

Tyr Lys Asn Ala Thr Tyr Gly Tyr Val Leu Asp Asp Pro Asp Pro Asp
        130                 135                 140

Asp Gly Phe Asn Tyr Lys Gln Met Met Val Arg Asp Glu Arg Arg Phe
145                 150                 155                 160

Lys Met Ala Asp Lys Asp Gly Asp Leu Ile Ala Thr Lys Glu Glu Phe
                165                 170                 175

Thr Ala Phe Pro His Pro Asp Glu Tyr Asp Tyr Met Lys Asp Ile Val
            180                 185                 190

Val Gln Glu Thr Met Glu Asp Ile Asp Lys Asn Ala Asp Gly Phe Ile
        195                 200                 205

Asp Leu Glu Glu Tyr Ile Gly Asp Met Tyr Ser His Asp Gly Asn Ala
    210                 215                 220

Asp Glu Pro Glu Trp Val Lys Thr Glu Arg Glu Gln Phe Val Glu Phe
225                 230                 235                 240

Arg Asp Lys Asn Arg Asp Gly Arg Met Asp Lys Glu Glu Thr Lys Asp
                245                 250                 255

Trp Ile Leu Pro Ser Asp Tyr Asp His Ala Glu Ala Glu Ala Arg His
            260                 265                 270

Leu Val Tyr Glu Ser Asp Gln Asn Lys Asp Gly Lys Leu Thr Lys Glu
        275                 280                 285

Glu Ile Val Asp Lys Tyr Asp Leu Phe Val Gly Ser Gln Ala Thr Asp
    290                 295                 300

Phe Gly Glu Ala Leu Val Arg His Asp Glu Phe
305                 310                 315
```

<210> SEQ ID NO 2
<211> LENGTH: 955
<212> TYPE: DNA
<213> ORGANISM: Hamster

```
<400> SEQUENCE: 2
atggacctgc gtcagtttct tctgtgcctg tccctgtgta cagcctttgc actgagcaag    60
cctactgaaa aaaggaccg agtacaccat gaacctcagc tcagcgacaa agttcacaac    120
gatgctcaga attttgacta tgaccatgat gccttcttgg gtgcagaaga agcaaagagt    180
tttgatcagc tgacaccaga agagagcaag gaaaggcttg gaaagattgt aagtaaaata    240
gatgacgaca aggatgggtt tgtcactgtg gatgaactca aaggctggat taagtttgca    300
caaaagcgct ggattcacga ggatgtagag cggcaatgga aggggcacga cctcaatgag    360
gatggcctcg tttcctggga ggagtataaa aatgccacct acggctacgt tttagatgat    420
ccagaccctg atgatggatt caattataaa cagatgatgg ttagagatga gcggaggttt    480
aaaatggcag acaaggatgg agacctgatt gccacaaagg aggaatttac cgcttttccg    540
caccctgatg agtatgacta catgaaagac atagttgtgc aggaaacaat ggaggatata    600
gacaagaatg ctgatggttt cattgatcta gaagagtata ttggtgacat gtacagtcat    660
gatgggaacg ctgatgagcc agagtgggtg aagacagagc gagaacagtt tgttgagttt    720
cgagataaga accgggatgg gaggatggac aaggaggaga ccaaagactg gatcctccct    780
tccgactatg accacgcaga ggccgaggcc aggcatctag tctacgagtc agaccaaaac    840
aaggatggca agcttaccaa ggaggagatt gtcgacaagt atgatttatt tgtgggcagc    900
caggccacag attttgggga ggccttagtg cgacacgatg agttctaagc tgcaa         955

<210> SEQ ID NO 3
<211> LENGTH: 19
<212> TYPE: DNA
<213> ORGANISM: Artificial Sequence
<220> FEATURE:
<223> OTHER INFORMATION: Synthetic Seqeunce

<400> SEQUENCE: 3
gaactcaaag gctggatta                                                 19

<210> SEQ ID NO 4
<211> LENGTH: 19
<212> TYPE: DNA
<213> ORGANISM: Artificial Sequence
<220> FEATURE:
<223> OTHER INFORMATION: Synthetic Seqeunce

<400> SEQUENCE: 4
tcacaacgat gctcagaat                                                 19

<210> SEQ ID NO 5
<211> LENGTH: 19
<212> TYPE: DNA
<213> ORGANISM: Artificial Sequence
<220> FEATURE:
<223> OTHER INFORMATION: Synthetic Seqeunce

<400> SEQUENCE: 5
tcattgatct agaagagta                                                 19

<210> SEQ ID NO 6
<211> LENGTH: 19
<212> TYPE: DNA
<213> ORGANISM: Artificial Sequence
<220> FEATURE:
<223> OTHER INFORMATION: Synthetic Seqeunce
```

```
<400> SEQUENCE: 6
agacatagtt gtgcaggaa                                                      19

<210> SEQ ID NO 7
<211> LENGTH: 39
<212> TYPE: DNA
<213> ORGANISM: Artificial Sequence
<220> FEATURE:
<223> OTHER INFORMATION: Synthetic Seqeunce

<400> SEQUENCE: 7
aaaaaaaagc ttgccgccac catgggcacc acctggagg                                 39

<210> SEQ ID NO 8
<211> LENGTH: 33
<212> TYPE: DNA
<213> ORGANISM: Artificial Sequence
<220> FEATURE:
<223> OTHER INFORMATION: Synthetic Seqeunce

<400> SEQUENCE: 8
aaaaaatcta gagggctttt tgaccttgtg ttc                                       33

<210> SEQ ID NO 9
<211> LENGTH: 14
<212> TYPE: PRT
<213> ORGANISM: Artificial Sequence
<220> FEATURE:
<223> OTHER INFORMATION: Synthetic Seqeunce

<400> SEQUENCE: 9

Lys Ala Ala Arg Ala Arg Asn Glu Asp Tyr Arg Ala Leu Cys
 1               5                  10

<210> SEQ ID NO 10
<211> LENGTH: 19
<212> TYPE: PRT
<213> ORGANISM: Artificial Sequence
<220> FEATURE:
<223> OTHER INFORMATION: Synthetic Seqeunce

<400> SEQUENCE: 10

Tyr Ala Leu His Val Lys Ala Ala Arg Ala Arg Asp Arg Asp Tyr Arg
 1               5                  10                  15

Ala Leu Cys

<210> SEQ ID NO 11
<211> LENGTH: 36
<212> TYPE: DNA
<213> ORGANISM: Artificial Sequence
<220> FEATURE:
<223> OTHER INFORMATION: Synthetic Seqeunce

<400> SEQUENCE: 11
ggatccgccg ccaccatgca gcgcgtgaac atgatc                                    36

<210> SEQ ID NO 12
<211> LENGTH: 26
<212> TYPE: DNA
<213> ORGANISM: Artificial Sequence
<220> FEATURE:
<223> OTHER INFORMATION: Synthetic Seqeunce

<400> SEQUENCE: 12 ggatccccttt cattaagtga gctttg                                              26
```

```
<210> SEQ ID NO 13
<211> LENGTH: 29
<212> TYPE: DNA
<213> ORGANISM: Artificial Sequence
<220> FEATURE:
<223> OTHER INFORMATION: Synthetic Seqeunce

<400> SEQUENCE: 13
aagcctgaga tcaataagaa atgttcagg                                    29

<210> SEQ ID NO 14
<211> LENGTH: 29
<212> TYPE: DNA
<213> ORGANISM: Artificial Sequence
<220> FEATURE:
<223> OTHER INFORMATION: Synthetic Seqeunce

<400> SEQUENCE: 14
gacaaggatg gagacctcat tgccaccaa                                    29

<210> SEQ ID NO 15
<211> LENGTH: 29
<212> TYPE: DNA
<213> ORGANISM: Artificial Sequence
<220> FEATURE:
<223> OTHER INFORMATION: Synthetic Seqeunce

<400> SEQUENCE: 15
tggacctgcg acagtttctt atgtgcctg                                    29

<210> SEQ ID NO 16
<211> LENGTH: 29
<212> TYPE: DNA
<213> ORGANISM: Artificial Sequence
<220> FEATURE:
<223> OTHER INFORMATION: Synthetic Seqeunce

<400> SEQUENCE: 16
caccagaaga gagcaaggaa aggcttgga                                    29

<210> SEQ ID NO 17
<211> LENGTH: 50
<212> TYPE: DNA
<213> ORGANISM: Artificial Sequence
<220> FEATURE:
<223> OTHER INFORMATION: Synthetic Seqeunce

<400> SEQUENCE: 17
gtgcggaccc gcttccggtt gggcggtgct tgcgcgcgtg agctgagccg             50

<210> SEQ ID NO 18
<211> LENGTH: 51
<212> TYPE: DNA
<213> ORGANISM: Artificial Sequence
<220> FEATURE:
<223> OTHER INFORMATION: Synthetic Seqeunce

<400> SEQUENCE: 18
gtgggtgagc ggcggccacg gcatcctgtg ctgtggggc tacgaggaaa g            51

<210> SEQ ID NO 19
<211> LENGTH: 25
<212> TYPE: DNA
<213> ORGANISM: Artificial Sequence
<220> FEATURE:
<223> OTHER INFORMATION: Synthetic Seqeunce
```

<400> SEQUENCE: 19
gtaagtacgg tgatgcccag cccct                                   25

<210> SEQ ID NO 20
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 20
ttaactgctt ttcattttct tcaag                                   25

<210> SEQ ID NO 21
<211> LENGTH: 232
<212> TYPE: DNA
<213> ORGANISM: Artificial Sequence
<220> FEATURE:
<223> OTHER INFORMATION: Synthetic Seqeunce

<400> SEQUENCE: 21
atctaattat catggacctg cgacagtttc ttatgtgcct gtccctgtgc acagcctttg    60
ccttgagcaa acccacagaa aagaaggacc gtgtacatca tgagcctcag ctcagtgaca   120
aggttcacaa tgatgctcag agttttgatt atgaccatga tgccttcttg ggtgctgaag   180
aagcaaagac ctttgatcag ctgacaccag aagagagcaa ggaaaggctt gg           232

<210> SEQ ID NO 22
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 22
gtaaggtacc acctctcagg ggtct                                   25

<210> SEQ ID NO 23
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 23
ctggatttct ctgcattttc tacag                                   25

<210> SEQ ID NO 24
<211> LENGTH: 194
<212> TYPE: DNA
<213> ORGANISM: Artificial Sequence
<220> FEATURE:
<223> OTHER INFORMATION: Synthetic Seqeunce

<400> SEQUENCE: 24
aaagattgta agtaaaatag atggcgacaa ggacgggttt gtcactgtgg atgagctcaa    60
agactggatt aaatttgcac aaaagcgctg gatttacgag gatgtagagc gacagtggaa   120
ggggcatgac ctcaatgagg acggcctcgt ttcctgggag gagtataaaa atgccaccta   180
cggctacgtt ttag                                              194

```
<210> SEQ ID NO 25
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 25
gtaggtccct actgtctggg ggaaa                                           25

<210> SEQ ID NO 26
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 26
tttgacctaa atttttgttt tctag                                           25

<210> SEQ ID NO 27
<211> LENGTH: 167
<212> TYPE: DNA
<213> ORGANISM: Artificial Sequence
<220> FEATURE:
<223> OTHER INFORMATION: Synthetic Seqeunce

<400> SEQUENCE: 27
atgatccaga tcctgatgat ggatttaact ataaacagat gatggttaga gatgagcgga     60
ggtttaaaat ggcagacaag gatggagacc tcattgccac caaggaggag ttcacagctt    120
tcctgcaccc tgaggagtat gactacatga aagatatagt agtacag                  167

<210> SEQ ID NO 28
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 28
gtgggtgaga tgaaggattc tgaac                                           25

<210> SEQ ID NO 29
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 29
tctcttctta ttctttcctg tttag                                           25

<210> SEQ ID NO 30
<211> LENGTH: 61
<212> TYPE: DNA
<213> ORGANISM: Artificial Sequence
<220> FEATURE:
<223> OTHER INFORMATION: Synthetic Seqeunce

<400> SEQUENCE: 30
gaaacaatgg aagatataga taagaatgct gatggtttca ttgatctaga agagtatatt     60
g                                                                     61
```

```
<210> SEQ ID NO 31
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 31
gtaagtctct gcttttagtg ttttt                                           25

<210> SEQ ID NO 32
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 32
tttgtatgta tgtctgtgta cccag                                           25

<210> SEQ ID NO 33
<211> LENGTH: 200
<212> TYPE: DNA
<213> ORGANISM: Artificial Sequence
<220> FEATURE:
<223> OTHER INFORMATION: Synthetic Seqeunce

<400> SEQUENCE: 33
gtgacatgta cagccatgat gggaatactg atgagccaga atgggtaaag acagagcgag     60
agcagtttgt tgagtttcgg gataagaacc gtgatgggaa gatggacaag gaagagacca    120
aagactggat ccttccctca gactatgatc atgcagaggc agaagccagg cacctggtct    180
atgaatcaga ccaaaacaag                                                200

<210> SEQ ID NO 34
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 34
gtaagtctgg cgaggcccac acgct                                           25

<210> SEQ ID NO 35
<211> LENGTH: 25
<212> TYPE: DNA
<213> ORGANISM: Artificial Sequence
<220> FEATURE:
<223> OTHER INFORMATION: Synthetic Seqeunce

<400> SEQUENCE: 35
aattcattgc tatctctact ttcag                                           25

<210> SEQ ID NO 36
<211> LENGTH: 2411
<212> TYPE: DNA
<213> ORGANISM: Artificial Sequence
<220> FEATURE:
<223> OTHER INFORMATION: Synthetic Seqeunce

<400> SEQUENCE: 36
gatggcaagc ttaccaagga ggagatcgtt gacaagtatg acttatttgt tggcagccag     60
gccacagatt tggggaggc cttagtacgg catgatgagt tctgagctac ggaggaaccc    120
```

-continued

```
tcatttcctc aaaagtaatt tattttaca gcttctggtt tcacatgaaa ttgtttgcgc        180
tactgagact gttactacaa acttttaag acatgaaaag gcgtaatgaa aaccatcccg        240
tccccattcc tcctcctctc tgagggactg gagggaagcc gtgcttctga ggaacaactc      300
taattagtac acttgtgttt gtagatttac actttgtatt atgtattaac atggcgtgtt     360 tattttgta tttttctctg gttgggagta tgatatgaag gatcaagatc ctcaactcac      420
acatgtagac aaacattagc tctttactct ttctcaaccc cttttatgat tttaataatt     480
ctcacttaac taattttgta agcctgagat caataagaaa tgttcaggag agaggaaaga    540 aaaaaatat atgctccaca atttatattt agagagagaa cacttagtct tgcctgtcaa      600
aaagtccaac atttcatagg tagtagggc cacatattac attcagttgc tataggtcca     660
gcaactgaac ctgccattac ctgggcaagg aaagatccct ttgctctagg aaagcttggc     720
ccaaattgat tttcttcttt tccccctgt aggactgact gttggctaat tttgtcaagc     780
acagctgtgg tgggaagagt tagggccagt gtcttgaaaa tcaatcaagt agtgaatgtg    840
atctctttgc agagctatag atagaaacag ctggaaaact aaaggaaaaa tacaagtgtt    900 ttcgggcat acatttttt tctgggtgtg catctgttga aatgctcaag acttaattat      960
ttgccttttg aaatcactgt aaatgccccc atccggttcc tcttcttccc aggtgtgcca   1020
aggaattaat cttggtttca ctacaattaa aattcactcc tttccaatca tgtcattgaa   1080 agtgcccttta acgaaagaaa tggtcactga atgggaattc tcttaagaaa ccctgagatt   1140 aaaaaagac tatttggata acttatagga aagcctagaa cctcccagta gagtggggat     1200 tttttcttc ttccctttct cttttggaca atagttaaat tagcagtatt agttatgagt    1260
ttggttgcag tgttcttatc ttgtgggctg atttccaaaa accacatgct gctgaattta   1320
ccagggatcc tcatacctca caatgcaaac cacttactac caggccttt tctgtgtcca    1380 ctggagagct tgagctcaca ctcaaagatc agaggaccta cagagagggc tctttggttt   1440
gaggaccatg gcttaccttt cctgcctttg acccatcaca ccccattcc tcctctttcc    1500 ctctccccgc tgccaaaaa aaaaaaag gaaacgttta tcatgaatca acagggtttc     1560
agtccttatc aaagagagat gtggaaagag ctaagaaaac caccctttgt tcccaactcc   1620
actttaccca tatttatgc aacacaaaca ctgtccttt gggtccctt cttacagatg    1680 gacctcttga gaagaattat cgtattccac gttttagcc ctcaggttac caagataaat    1740
atatgtatat ataaccttta ttattgctat atctttgtgg ataatacatt caggtggtgc    1800
tgggtgattt attataatct gaacctaggt atatcctttg gtcttccaca gtcatgttga   1860
ggtgggctcc ctggtatggt aaaaagccag gtataatgta acttcacccc agcctttgta   1920
ctaagctctt gatagtggat atactctttt aagtttagcc ccaatatagg gtaatggaaa   1980
tttcctgccc tctgggttcc ccatttttac tattaagaag accagtgata atttaataat   2040
gccaccaact ctggcttagt taagtgagag tgtgaactgt gtggcaagag agcctcacac   2100
ctcactaggt gcagagagcc caggccttat gttaaaatca tgcacttgaa aagcaaacct   2160
taatctgcaa agacagcagc aagcattata cggtcatctt gaatgatccc tttgaaattt   2220
tttttttgtt tgtttgttta aatcaagcct gaggctggtg aacagtagct acacacccat   2280
attgtgtgtt ctgtgaatgc tagctctctt gaatttggat attggttatt ttttatagag   2340
tgtaaaccaa gttttatatt ctgcaatgcg aacaggtacc tatctgtttc taaataaaac   2400
tgtttacatt c                                                        2411
```

```
<210> SEQ ID NO 37
<211> LENGTH: 50
<212> TYPE: DNA
<213> ORGANISM: Artificial Sequence
<220> FEATURE:
<223> OTHER INFORMATION: Synthetic Seqeunce

<400> SEQUENCE: 37
attatggggt atgtatgacc ttcattttcc aagaaataga actctagctt            50
```

COMPOSITIONS AND METHODS FOR INCREASING PRODUCTION OF RECOMBINANT GAMMA-CARBOXYLATED PROTEINS

The present application is §371 application of PCT/US2006/061575 filed 4 Dec. 2006 which claims priority to U.S. 60/742,076 filed 2 Dec. 2005 and U.S. 60/782,056 filed 14 Mar. 2006, the entire disclosure of each being incorporated by reference herein.

Pursuant to 35 U.S.C. §202 (c) it is acknowledged that the U.S. Government has certain rights in the invention described, which was made in part with funds from the National Institutes of Health, Grant Number HL69331.

FIELD OF THE INVENTION

This invention relates to the fields of medicine and blood coagulation disorders. More specifically the invention provides genetically engineered cell lines useful for high level production of proteins requiring gamma carboxylation for function, including but not limited to human clotting factors IX and VII.

BACKGROUND OF THE INVENTION

Several publications and patent documents are cited throughout the specification in order to describe the state of the art to which this invention pertains. Each of these citations is incorporated by reference herein as though set forth in full.

Recombinant factors VII, VIIa, VIII, IX, and protein C are important pharmaceuticals useful in the treatment of traumatic bleeding complications (6), hemophilia (7), and sepsis (8). These proteins play important roles in the coagulation cascade (39), which comprises plasma and membrane proteins that are responsible for arrest of blood loss at sites of injury.

Factors VII, IX, and protein C belong to a family of vitamin K-dependent proteins that are modified post-translationally to contain γ-carboxyglutamic acid (Gla), Ca++ binding amino acid residues (2). The modification is carried out by the vitamin K-dependent γ-carboxylation system located in the endoplasmic reticulum (ER) (2). Two essential enzymes of the system are 1) the vitamin K-dependent γ-carboxylase, an integral membrane protein of 92 kDA which requires reduced vitamin K (vit.$K_1H_2$) as cofactor and 2) the warfarin sensitive enzyme vitamin K 2,3-epoxide reductase (VKOR), which produces the cofactor (2).

A major problem with production of recombinant vitamin K-dependent coagulation factors for use as pharmaceuticals has been poor recovery of functional proteins from the cell medium (9). It has been shown that poor recovery results from, 1) incomplete γ-carboxylation of the secreted proteins (9) and 2) incomplete removal of the propeptide by the protease PACE/furin in the Golgi apparatus. Incomplete γ-carboxylation is a significant problem as <10% of the secreted recombinant vitamin K-dependent proteins have been reported to be fully γ-carboxylated and functional (9). It is believed that incomplete γ-carboxylation occurs when an excess of newly synthesized precursors of vitamin K-dependent proteins appear in the ER and exceed the capacity of the cell's γ-carboxylation system to fully modify all of the precursors (9).

Clearly, a need exists for improved methods for producing high levels of the coagulation factors discussed above. It is an object of the invention to provide such methods.

SUMMARY OF THE INVENTION

In accordance with the present invention, a method for the increased production of gamma-carboxylated proteins of interest is provided. An exemplary method comprises providing a cell line which has been recombinantly engineered to over-express VKORC1 and introducing a nucleic acid encoding the gamma-carboxylated protein of interest into the VKORC1 overexpressing cells under conditions wherein protein encoded by said nucleic acid is produced in enhanced yield relative to cells which do not overexpress VKORC1.

In yet another aspect, the method includes introducing a molecule into the cell which down regulates or inhibits calumenin function. In a preferred embodiment, siRNA molecules effective to reduce expression of calumenin are introduced into VKORC1-overexpressing cells. In another embodiment, antisense molecules which effectively down regulate calumenin expression may be employed for this purpose. Alternatively, cells from a calumenin knockout animal which also optionally overexpress VKORC1 can be utilized. In yet another aspect, calumenin mutant proteins exist which exhibit reduced function (e.g. calumenin wherein the arginine at position 4 in the signal peptide has been replaced with a glutamine). Accordingly, cells comprising such mutants and VKORC1 can be utilized in the methods disclosed herein. Gamma-carboxylated proteins which may be produced in enhanced yield according the methods of the invention, include, without limitation, hFIX, hFVII, hFX, protein C, protein S, Protein Z, growth arrest protein 6 (GAS6), PRGP1, PRGP2, TmG3, TmG4, osteocalcin and matrix Gla protein (MGP). The method can also include, isolation and optionally purification of the gamma-carboxylated protein. Also encompassed by the invention are methods of treating a patient having a blood coagulation disorder with a gamma-carboxylated coagulation protein produced using the methods disclosed herein.

In yet another embodiment of the invention, improved cell lines which produce gamma carboxylated proteins in high yield are provided. A preferred embodiment of the invention comprises an immortalized cell line for the production of gamma-carboxylated proteins containing a vector expressing VKORC1, molecules which down regulate calumenin function (e.g., calumenin specific siRNA molecules, calumenin specific antisense molecules,) and a nucleic acid encoding a gamma-carboxylated protein of interest. Alternatively, the overexpressing VKORC1 cell line may further comprise a vector expressing mutated calumenin. Finally, cells obtained from a calumenin knock out animal can be immortalized and further transfected with VKORC1 to enhance production of gamma carboxylated proteins. In a particularly preferred embodiment, the cell lines comprise BHK cells which overexpress Factor IX or Factor VII.

Also encompassed by the present invention are plant cells and plants derived therefrom which have been genetically engineered to optionally express VKCOR1, a gamma-carboxylase, a gamma-carboxylated protein of interest and siRNA or calumenin-specific antisense molecules effective to reduce calumenin function or a plant homolog thereof. Additionally, calumenin expression in such cells can be absent or downregulated with the various protocols disclosed herein.

BRIEF DESCRIPTION OF THE DRAWINGS

FIGS. 8A and 8B show the protein (SEQ ID NO: 1) and cDNA sequences (SEQ ID NO: 2) of calumenin isolated from hamster. Antisense molecules which span the translational start site of cDNA sequence can also be used to down regulate calumenin expression.

DETAILED DESCRIPTION OF THE INVENTION

Figure 1:
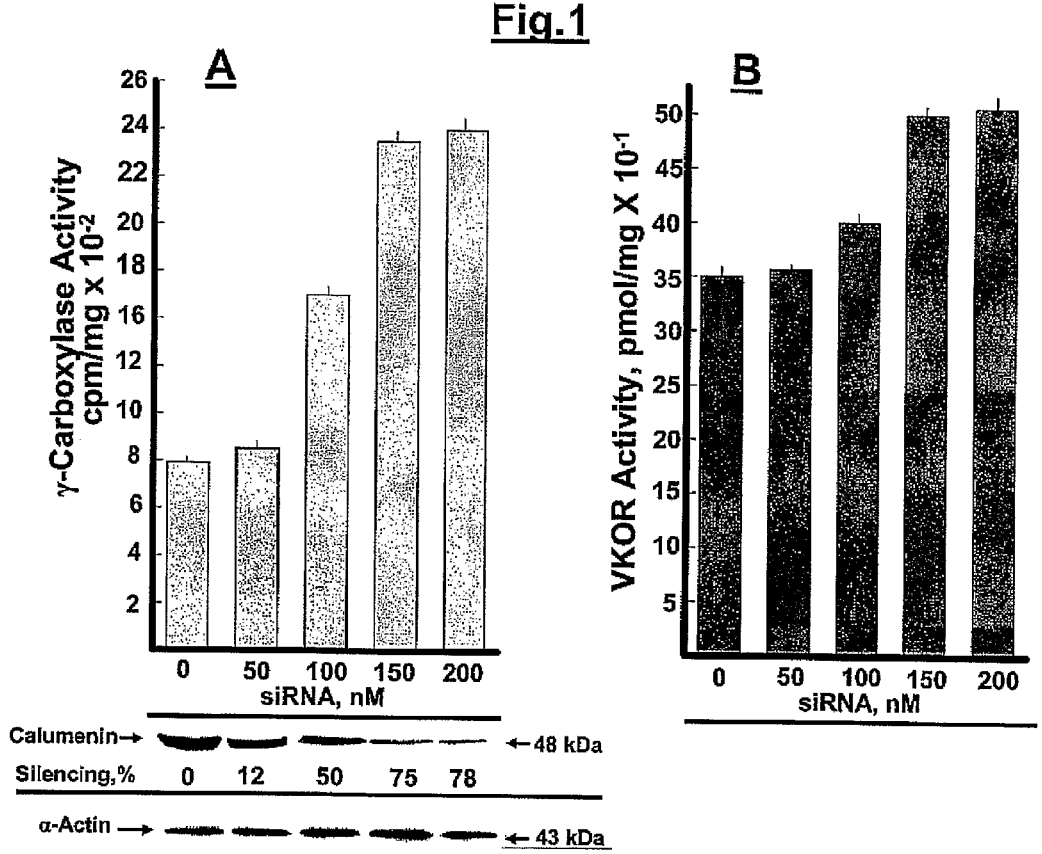
FIG. 1 shows the effect of calumenin siRNA silencing on enzyme activities of the vitamin K-dependent γ-carboxylation system. BHK cells engineered to overexpress r-hFIX and VKORC1 were transfected with the various concentrations of siRNA SMART pool against hamster calumenin shown in the figure (see Experimental Procedures). After 48 hours, cells were harvested and tested for FLEEL γ-carboxylase activity triggered with chemically reduced vitamin $K_1H_2$ (panel A) and VKOR activity (panel B). Each bar represents the average activity of three parallel incubations and standard deviations are shown on top of the bars. Western blots of calumenin (48 kDa) present in the various siRNA SMART pool treated cells are shown as well as silencing of calumenin in % of the control with no siRNA. Western blotting of α-Actin verifies equal protein loading in the various lanes.

Certain recombinant vitamin K-dependent blood coagulation factors (factors VII, IX and protein C) are valuable pharmaceutical agents for the treatment of bleeding complications. Because of their vitamin K-dependent post translational modification, their synthesis by eukaryotic cells is essential. The eukaryotic cell harbors a vitamin K-dependent γ-carboxylation system that converts the proteins to γ-carboxyglutamic acid (Gla) containing proteins. However, the system in eukaryotic cells has limited capacity and cell lines over expressing vitamin K-dependent clotting factors produce only a fraction of the recombinant proteins as fully γ-carboxylated, physiologically competent proteins. In the present invention, we have used recombinant human factor IX (r-hFIX) producing cells, engineered to stably overexpress various components of the cell's γ-carboxylation system, to determine if increased production of functional r-hFIX can be accomplished. The BHK cell lines tested secreted the same amount of r-hFIX into serum free medium ($16\pm2$ μm/day/$10^6$ cells). Overexpression of γ-carboxylase is shown to inhibit production of functional r-hFIX. On the other hand, cells over expressing VKORC1, the reduced vitamin K cofactor producing enzyme of the vitamin K-dependent γ-carboxylation system, produced 2.9-fold more functional r-hFIX than control BHK cells. The data are consistent with the notion that VKORC1 is the rate limiting step in the system and is a key regulatory protein in synthesis of active vitamin K-dependent proteins. The data indicate that over expression of VKORC1 can be utilized for increased cellular production of recombinant vitamin K-dependent proteins.

In yet another aspect of the invention, it has been discovered that reducing or inhibiting expression and/or function of the γ-carboxylation inhibitor calumenin also dramatically increases expression of functional r-hFIX in cells optionally overexpressing VKORC1. Calumenin specific siRNAs or antisense molecules are suitable for this purpose. Alternatively mutants of calumenin which lack function can also be utilized. Finally, the cell lines of the invention can be incubated in the presence of therapeutic agents which specifically down regulate calumenin function, thereby increasing the yield of gamma-carboxylated proteins.

The invention also includes methods of administration of an effective amount of the gamma-carboxylated proteins produced using the cell lines disclosed herein to a patient in need thereof. Certain proteins described herein modulate the blood coagulation cascade. Accordingly, once produced and purified, they can be used to advantage to treat patients suffering from hemophilia, traumatic bleeding, stroke, sepsis or thrombus formation.

In yet another embodiment, plant cells are utilized to produce the gamma-carboxylated proteins of the invention. Introduction of heterologous proteins into plant cells can be achieved using PEG-fusion, biolistic delivery of exogenous DNA, or Agrobacterium mediated gene transduction. Recombinant methods for introducing heterologous nucleic acids into plant cells are well known to those of skill in the art. See for example, Current Protocols of Molecular Biology. Ausubel et al. eds. Plant cells will be engineered to express gamma-carboxylase, the gamma-carboxylated protein of interest and optionally, calumenin siRNAs. Plants regenerated from the plant cells described above are also within the scope of the invention.

Given the role played by calumenin in gamma-carboxylated protein production, whole animal models to study calumenin function are highly desirable. Thus, the invention also provides animals which are transgenic for calumenin expression.

The availability of calumenin encoding nucleic acids enables the production of strains of laboratory mice carrying part or all of the calumenin gene or mutated sequences thereof. Such mice provide an in vivo model for studying calumenin function. Alternatively, the calumenin sequence information provided herein enables the production of knockout mice in which the endogenous gene encoding calumenin has been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role calumenin plays in embryonic development and gamma-carboxylation of proteins.

A transgenic mouse carrying the human calumenin gene is generated by direct replacement of the mouse calumenin gene with the human gene. These transgenic animals are useful for drug screening studies as animal models for human diseases and for identifying agents which modulate gamma carboxylation.

A transgenic animal carrying a "knock out" of calumenin is useful for assessing the role of calumenin in gamma carboxylation reactions. As yet another means to define the role that calumenin plays in mammalian systems, mice can be generated that cannot make calumenin protein because of a targeted mutational disruption of the calumenin gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA.

The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered calumenin gene generally should not fully encode the same calumenin protein native to the host animal and its expression product should be altered to a minor or great degree, or absent altogether. However, it is conceivable that a more modestly modified calumenin gene will fall within the scope of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated calumenin genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

In yet another approach, transgenic mice can be produced using technology provided in U.S. Pat. Nos. 5,464,764 and 4,959,317 which describe the PNS method discussed above coupled with Cre-lox technology.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Therapeutic agents which modulate calumenin function may be screened in studies using calumenin transgenic mice.

In another embodiment of the invention, calumenin knock-out mice may be used to produce an array of monoclonal antibodies specific for calumenin protein.

As mentioned, several different gamma-carboxylated proteins can be produced using the cell line based methods described herein. The Genbank accession numbers for certain of these proteins are provided below.

| | |
|---|---|
| 1) Rat gamma-carboxylase: | gi:6136262 |
| 2) Rat VKORC1 | gi:42627871 |
| 3) Human Factor IX | gi:825656 |
| 4) Human Prothrombin | gi:339641 |
| 5) Human Factor VII | gi:10518503 |
| 6) Human Protein C | gi:190323 |
| 7) Human Protein S | gi:190449 |
| 8) Human Protein Z | gi:6116779 |
| 9) Human GAS6 | gi:45576177 |
| 10) Human PRGP1 | gi:20140420 |
| 11) Human PRGP2 | gi:4506137 |
| 12) Human TmG3 | gi:31543811 |
| 13) Human TmG4 | gi:13129074 |
| 14) Human MGP | gi:47496663 |
| 15) Human Osteocalcin | gi:40316933 |

Definitions

The phrase "gamma-carboxylated protein" as used herein refers to a class of proteins for which gamma-carboxylation is essential or enhances protein function. Such proteins include, without limitation, hFIX, hFVII, hFX, protein C, protein S, Protein Z, growth arrest protein 6 (GAS6), PRGP1, PRGP2, TmG3, TmG4, osteocalcin and matrix Gla protein (MGP).

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently. Thus, the nucleic acids of the invention may be transiently or constitutively expressed in host cells.

The term "selectable marker gene" refers to a gene that when expressed confers a selectable phenotype, such as antibiotic resistance, on a transformed cell or plant.

A "coding sequence" or "coding region" refers to a nucleic acid molecule having sequence information necessary to produce a gene product, when the sequence is expressed.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase. Promoters may drive expression of an operably linked coding sequence constitutively. Alternatively, inducible promoters which drive expression of an operably linked coding region upon stimulation with an inducing agent are also suitable for use in the invention. Promoters which drive expression of an operably linked coding sequence in a tissue specific manner (e.g., in the liver or endothelial cell) are known to those of skill in the art and can also be used in the methods of the present invention.

A "cell line" is a clone of a primary cell or cell population that is capable of stable growth in vitro for many generations. Many cell lines may be used in accordance with the present invention. These include, without limitation, CHO, BHK, human kidney 293, Mouse C127, HeLa, 3T3, and MDCK. All of the cell lines listed are available from the American Tissue Type Collection.

The phrase "down regulation of calumenin expression" refers to the process of inhibiting or preventing expression of calumenin encoding nucleic acids or calumenin protein, thereby increasing the yield of gamma carboxylated proteins in VKCOR1 over-expressing cells. Calumenin expression can be down regulated using siRNA or antisense based technologies. Alternatively, cells can be obtained from calumenin knock-out animals, transfected with VKCOR1 and optionally immortalized. Calumenin from hamster has been sequenced. See GenBank accession number gi:63148518 and FIGS. 8A and 8B. Suitable antisense molecules can be designed which are optimally between 15 and 45 nucleotides in length, more preferably 20-30 nucleotides in length which hybridize the translational start site of calumenin encoding nucleic acid. Alternatively, the sequence information provided in FIG. 8 facilitates the production of calumenin knock out animals from which cells may be obtained for use in the methods of the present invention. Additionally mutants of calumenin are known in the art which exhibit reduced calumenin function. The use of such mutants is within the scope of the present invention.

The following examples are provided to illustrate certain embodiments of the invention. They are not intended to limit the invention in any way.

EXAMPLE

Cell lines for improving production yield of hFIX

The following materials and methods are provided to facilitate the practice of Example 1.
Engineering of BHK Cell Lines Overexpressing r-hFIX and Proteins of the Vitamin K-Dependent γ-Carboxylation System:

Cloning of VKORC1 and γ-carboxylase cDNAs into the dual promoter vector plasmid pBUDCE4.1 (Invitrogen, Carlsbad, Calif.) and construction of the pLXIN retroviral vector (Clontech, Palo, Ca.) containing a human FIX construct as well as selection of clones of cells stably overexpressing the recombinant proteins are published in recent articles from our laboratory. As documented in the published studies (11, 17), it was found that BHK cells stably overexpressing r-hFIX and VKORC1 produced the highest amount of functional r-hFIX. These cells were selected for the studies described in this work.
Silencing of the γ-Carboxylation Inhibitor Calumenin in BHK Cells:

Hamster calumenin was cloned by our laboratory using standard technology and the cDNA sequenced on both strands. The sequence has been deposited in Gene Bank under the accession # gi:63148518. We provided DHARMACON, RNA Technologies, Lafayette, Colo. with the hamster calumenin cDNA sequence and ordered the siRNA SMART pool containing 50 nmols of a mixture of 4 oligonucleotides with potential for hamster calumenin mRNA destruction by RISC complexes. The four oligonucleotides have the following sequences:

| | |
|---|---|
| GAACTCAAAGGCTGGATTA | (SEQ ID NO: 3) |
| TCACAACGATGCTCAGAAT | (SEQ ID NO: 4) |
| TCATTGATCTAGAAGAGTA | (SEQ ID NO: 5) |
| AGACATAGTTGTGCAGGAA | (SEQ ID NO: 6) |

Transfection of the VKORC1+r-hFIX overproducing BHK cell line with the siRNA SMART pool oligonucleotides was carried out with Lipofectamine (Invitrogen, Carlsbad, Calif.) according to the protocol provided by the company. SiRNA against human GAPDH was used as a positive control and a negative control consisted of a mixture of 4 scrambled siR- NAs. Following transfection, cells were grown in DMEM containing 10% fetal bovine serum, 500 µg/ml G418 and 400 µg/ml Zeocin for 24 hours. The attached cells were then washed 2× with PBS and continued growing in DMEM without serum but with the addition of 5 µg/ml of vitamin K1 (AquaMEPHYTON, MERCK & CO; INC, Whitehouse, N.J.). After 24 hours in the serum free medium, medium was collected for r-hFIX purification and cells harvested for VKOR and γ-carboxylase activity measurements.

Figure 7:
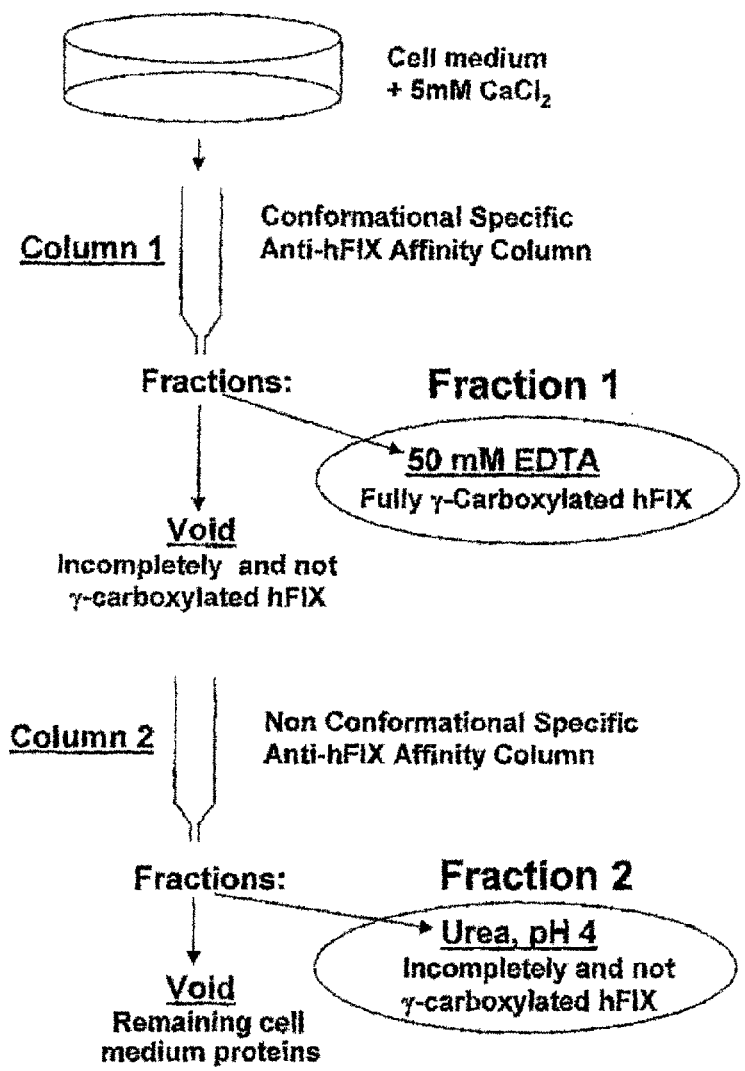
FIG. 7 shows a flow scheme of immunoaffinity chromatography purification of functional and non functional r-hFIX from serum free media from engineered BHK cells. Individual media from BHK cells stably expressing r-hFIX and the various protein components of the vitamin K-dependent γ-carboxylation system were chromatographed on columns 1 and 2 as described below. Column 1 has conformational specific anti-hFIX antibodies attached which, in the presence of $Ca^{++}$, retains fully γ-carboxylated and functional r-hFIX. These variants of r-hFIX are eluted from the column with 50 mM EDTA and appear in Fraction 1. Column 2 has non-conformational specific anti-hFIX antibodies attached which retain the remaining non-functional r-hFIX present in the void volume fraction (VOID) from column 1. These variants of r-hFIX are released with urea, pH 4 as described in below and appear in Fraction 2.
Figure 9:
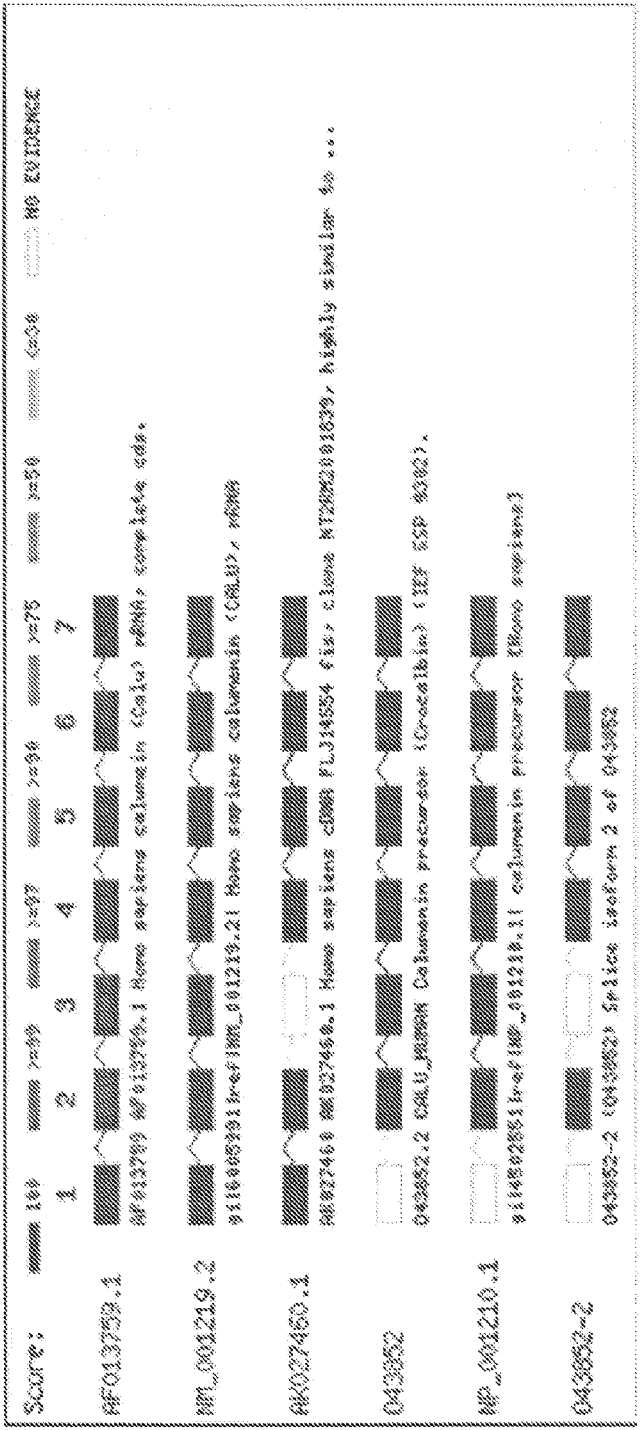
FIG. 9 shows the genomic sequence of human calumenin. The intron/exon boundaries of the seven exon sequences are shown. Antisense molecules of approximately 15-50 nucleotides which hybridize to the intron/exon boundaries can be designed which are effective to down regulate calumenin expression, thereby enhancing gamma-carboxylated protein production. Another suitable target encompasses the translational start site.

Purification of Functional and Non Functional r-hFIX from Cell Medium:

Preparation of conformational specific and non conformational specific immunoaffinity columns for purification of functional and non functional r-hFIX respectively has been described recently by our laboratory for use in a tandem designed chromatography system for isolation of the two different pools of r-hFIX (11). Briefly, γ-carboxylated r-hFIX that was able to undergo the $Ca^{2+}$-induced conformational change, characteristic of fully γ-carboxylated functional plasma factor IX, was purified from the cell medium by immunoaffinity chromatography on a column with hFIX conformational-specific antibodies as immobilized ligands. As indicated in the flow scheme shown in FIG. 7, these variants of r-hFIX were retained by and eluted from column 1 with 50 mM EDTA (Fraction 1). Recombinant hFIX proteins that were unable to undergo this conformational change appeared in the void volume traction (Void) from column 1. These variants of cell-produced r-hFIX were purified on an immunoaffinity column (column 2) with nonconformational-specific hFIX antibodies as immobilized ligands. They were eluted from the column with urea, pH 4, which resulted in Fraction 2 (FIG. 7). Thus, purification of fully γ-carboxylated r-hFIX, with coagulation factor activity, is based upon the conformational change the Gla region in the protein undergoes in the presence of Ca++ and the availability of antibodies that specifically recognize the Ca++ induced conformation (9,11). The non functional r-hFIX proteins in the medium is purified on an anti-human factor IX affinity column that recognizes all forms of human factor IX (11). Cellular production of functional r-hFIX is reported as % of total r-hFIX produced by the cells (11). As described in a previous article (11) digitized images of immunoreactive protein bands of functional r-hFIX and non functional r-hFIX on FUJI Medical X-Ray Film SuperRX (Fisher Scientific, Pittsburgh, Pa.) were analyzed with Kodak 1D software (Eastman Kodak, Rochester, N.Y.) to determine the integrated areas representing the protein bands. For determination of r-hFIX protein content, standard curves of Western blots with known purified human FIX were established and compared to unknown samples. All measurements were adjusted to be in the linear range of the standard curve.

Construction of an Expression Plasmid with c-myc Epitope Tagged VKORC1:

The oligonucleotides used for rat VKORC1 PCR were: Sense primer 5'-AAA AAA AAG CTT GCC GCC ACC ATG GGC ACC ACC TGG AGG-3'(SEQ ID NO: 7) (underlined bases to generate Hind III site; bases in italics were used to generate a Kozak sequence). The antisense primer was 5'-AAA AAA TCT AGA GGG CTT TTT GAC CTT GTG TTC-3' (SEQ ID NO: 8) (the underlined bases were used to generate a Xba I site. The stop codon was removed by adding the c-myc epitope).

The modified cDNA for rat VKORC1 was then cloned into the Hind III and Xba I site of the pBUDCE4.1 vector under the control of a CMV promoter. The Xba I site fused the rat VKORC1 in frame with the c-myc epitope. The c-myc peptide sequence is EQKLISEEDL. The recombinant plasmid with cDNA for rat c-myc tagged-VKORC1 was sequenced on both strands to eliminate any PCR errors.

Selection of BHK Cell Lines Expressing c-myc-Tagged VKORC1:

Plasmid pBUDCE4.1 with c-myc-tagged VKORC1 was used to transfect BHK21 cells (ATCC number CCL-10). Cells were transfected using the FuGENE 6 transfection reagent from Roche Applied Science, Indianapolis, Ind. according to the manufacture's recommendations. After 24 hours of transfection, cells were passaged at 1:20 dilution into fresh growth medium (DMEM containing 10% fetal bovine serum) with Zeocin antibiotic for selective pressure (Invitrogen, San Diego, Calif.) at a concentration of 400 µg/ml. Medium containing 400 µg/ml zeocin was changed after every 2-3 days for 6 weeks. After selection of stable cell lines expressing rat c-myc-tagged-VKORC1 fusion protein, the cells were maintained in the presence of 200 µg/ml of zeocin in DMEM containing 10% fetal bovine serum.

Animals:

Male Sprague Dawley rats weighing 250-300 g were purchased from Zivic Miller Laboratories, Inc., Pittsburgh, Pa. Rats were housed, fed and used for experiments as approved by the Animal Care and Use Committee at Wake Forest University School of Medicine. Liver microsomes were prepared as described by our laboratory (18).

Extraction of Microsomes:

For removal of microsomal luminal and peripherally bound membrane proteins, microsomes obtained from 4 g of rat liver were suspended in 8 ml of 100 mM $Na_2CO_3$, 1.2 M KCl, 0.025% deoxycholate, pH 11.5 with a Potter Elvehjelm glass homogenizer and centrifuged at 100,000×g for 45 min (14). The pellet was resuspended in 8 ml of 50 mM Tris base with the same homogenizer and centrifuged a second time at 100,000×g for 45 min. Pellets (extracted microsomes) were stored at −85° C. until used for experiments.

Enzyme Assays:

Warfarin sensitive VKOR activity was measured as described (19) by estimating the percent conversion of vitamin $K_1$ 2,3-epoxide (Vit.K>O) to vitamin $K_1$. The vitamin and the epoxide were separated on a reversed phase C18 column in 100% methanol and quantified against external standards. VKOR activity was either triggered with 5 mM DTT or 0.32 mM reduced RNAse. Reduced bovine RNAse was prepared according to a modified method originally described by Rupp et al. (20). One hundred mg RNAse was dissolved in 500 µl of 0.2 M Tris-Acetate, 6 M guanidinium hydrochloride, pH 8.0. Seventy-two mg DTT was added and the solution was left at 37° C. for one hour. Then the pH was adjusted to 4.0 with acetic acid and DTT, Tris and guanidinium hydrochloride removed by gel filtration on a column of Sephadex G-25 equilibrated in 0.1 M acetic acid. Prior to chromatography, the column resin and the 0.1 M acetic acid were saturated with $N_2$. The void volume fraction containing reduced RNAse was distributed into sealed 0.75 ml serum flasks filled with $N_2$ which were stored at 4° C. until use. Gamma-carboxylase activity was assayed as described (14) as $^{14}CO_2$ incorporation into the synthetic peptide FLEEL (FLEEL γ-carboxylation). The reaction was either triggered by adding chemically reduced vitamin $K_1H_2$ (Vit.$K_1H_2$) (100 µg/ml) to the assay mixture or triggered by VKOR produced reduced Vit.K1H2 by adding 0.5 mM reduced RNAse and 40 µMVit.K>O. Both carboxylase assays were carried out as described (14) with saturating FLEEL concentration for the reactions. The PDI inhibitor bacitracin was added to the assay mixtures in the concentrations specified in the brief description of the drawings. Stock solutions of bacitracin were prepared in distilled water. Blood clotting activities of purified r-hFIX and plasma hFIX were determined with the Activated Partial Thromboplastin Time (APPT) kit APTT-SP (liquid)-0020006300 from Instrumentation Laboratory, Lexington, Mass. In order to determine the specific activity of r-hFIX, a standard curve of dilutions of purified plasma hFIX was made. One unit of hFIX activity was defined as the activity of hFIX in one ml of pooled human plasma.

Immunoprecipitation, SDS-PAGE and Western Blotting:

Extracted microsomal membranes were resuspended in buffer D (250 mM sodium phosphate, 0.5 M KCl, 20% glycerol, 0.75% CHAPS, pH 7.85 containing 10 µg/ml of the Sigma Protease Inhibitor Cocktail for use with mammalian cell and tissue extracts) using a Dounce homogenizer. For blocking of free thiol groups, 20 mg NEM was added per ml of buffer D before homogenizing. The protein concentration was 6.8 mg/ml. Prior to immunoprecipitation, the soluble membrane proteins in buffer D were gel filtrated into RIPA buffer (50 mM Tris, 1% NP-40, 0.25% deoxycholate, 150 mM NaCl, 1 mM EDTA, pH 7.4 containing 10 µg/ml of the Sigma Protease Inhibitor Cocktail) and passed through an affinity column packed with a mixture of Sepharose-4B-Protein A and Sepharose-4B-Protein G equilibrated in RIPA buffer. The various antibodies that were used for immunoprecipitation were added to the pre-cleared samples at the concentrations specified in the figure legends. The mixtures were allowed to rotate overnight at 4° C. Depending on the antibody used for immunoprecipitation, Sepharose-Protein A or -Protein G beads were added to the samples respectively and the mixtures allowed to rotate for an additional 1 hour at 4° C. for binding of immune complexes to the beads. The beads were washed with RIM buffer and 50 mM Tris base before immune complexes were released from the beads by boiling them in SDS-PAGE buffer containing no reductant. The beads were removed by centrifugation and the supernatant prepared for SDS-PAGE either as oxidized samples or reduced samples prepared by boiling the supernatant with 5% ME for 2 minutes. For Western blotting, proteins were transferred to PVDF membranes and developed with antibodies as described (21) using the ECL plus detection system from Amersham Biosciences, Piscataway, N.J.

Immunoprecipitation of cell proteins was carried out as follows. Cells were washed and harvested in PBS and extracted with RIPA buffer containing 10 µg/ml of the Sigma protease inhibitor cocktail. Cell debris was removed by centrifugation and the supernatant pre-cleared by rotating it for 1 hour at 4° C. in the presence of a mixture of Sepharose 4B-Protein A and -Protein G beads. Addition of c-myc antibodies, isolation of immune complexes, SDS-PAGE and Western blotting were carried out as described above.

Materials:

Anti-PDI mouse monoclonal antibodies, cat # SPA-891, lot # B503461 were from Stressgen bioreagents, Victoria, British Colombia V8C 4B9, in Canada. Rabbit anti-rat VKORC1 antibodies made against the peptide epitope KAARARNEDYRALC (SEQ ID NO: 9) (17) were custom made by ALPHA Diagnostic, San Antonio, Tex. and affinity purified by our laboratory as described (17). Affinity purified rabbit peptide antibodies made against the peptide epitope YALHVKAARARDRDYRALC (SEQ ID NO: 10) from the human VKORC1 sequence were a kind gift from Dr. Allan Rettie, Department of Medicinal Chemistry, University of Washington, Seattle, Wash. C-myc antibodies and anti-human GAPDH antibodies were from Abcam Inc., Cambridge, Mass.

Protein A-Sepharose, Protein-G-Sepharose, bovine ribonuclease B (RNAse), scrambled RNAse, bacitracin and monolconal anti-α-Actin antibodies were from Sigma-Aldrich, St. Louis, Mo. Rabbit polyclonal affinity purified anti-calumenin antibodies were prepared by our laboratory as described (18). Bovine and human factor IX purified from plasma were purchased from Enzyme Research Laboratories, South Bend, Ind. All other chemicals used were of highest quality. Human liver microsomes were from CellxDirect, Pittsboro, N.C.

Cloning of Human Factor IX into the pLXIN Retroviral Vector:

Plasmid pCMV5FIX containing the full length human factor IX (hFIX) cDNA was purchased from American Type Culture Collection (Manassas, Va., Cat# 79871). BamHI restriction sites were generated at the 5' and 3' ends of hFIX cDNA using PCR in order to clone the cDNA into the pLXIN retroviral vector (Clontech, Palo, Ca.) for expression in mammalian cell lines. Kozak sequence was also generated at the 5' end of the hFIX cDNA. The oligonucleotides used for hFIX PCR were 1) sense primer: 5'-GGA TCC GCC GCC ACC ATG CAG CGC GTG AAC ATG ATC (SEQ ID NO: 11); and 2) anti-sense primer: 5'-GGA TCC CTT TCA TTA AGT GAG CTT TG-3' (SEQ ID NO: 12). Thirty five cycles of PCR were performed under the following conditions: Denature at 94° C. for 30 sec, anneal for 1 min. at 55° C. followed by an extension at 72° C. for 7 min. The modified cDNA for human factor IX was then cloned into the BamHI site of the pLXIN vector under control of the CMV promoter. Recombinant plasmid with cDNA for hFIX was sequenced on both strands to eliminate any PCR errors.

Retroviral Packing:

PG 13 cells (kind gift from Dr. Charles Morrow, Department of Biochemisty, Wake Forest University School of Medicine, Winston-Salem, N.C.) were transfected with the pLXIN retroviral vector containing the hFIX insert for packing. Retroviral particles were harvested from the PG 13 cell medium 72 hours post transfection. Harvested medium was centrifuged at 3000×g to remove cell debris. The supernatant was collected and used to infect BHK cells and BHK cells engineered to over express γ-carboxylase, VKORC1 and VKORC1+γ-carboxylase respectively. Stable r-hFIX producing cell lines were selected with G418.

Cell Culture:

Cells were seeded and grown in DMEM containing 10% fetal bovine serum, 500 µg/ml G418 and 400 µg/ml Zeocin. At confluency, the attached cells were washed 2× with PBS and continued growing in DMEM without serum but with the addition of 5 µg/ml of vitamin K1 (AquaMEPHYTON, MERCK & CO; INC, Whitehouse, NJ). After 24 hours the serum free medium was collected and used for purification of r-hFIX.

Preparation of hFIX Antibodies:

Purified human factor IX (HFIX 1009; 1.31 mg/ml) was purchased from Enzyme Research Laboratories, South Bend, Ind. Three hundred µg hFIX was emulsified in Freund's Complete Adjuvant (Sigma, St. Louis, Mo.) and used for intradermal injections in New Zeeland white female rabbits (Robinson Services Inc., Mocksville, N.C.). After 4 weeks, each rabbit was given a booster dose IP of 300 µg hFIX emulsified in Freund's Incomplete Adjuvant. One week after the booster dose, blood was drawn by air vein puncture. The rabbits were allowed to recover for 4 weeks before a second booster dose was given to obtain a second bleed. The entire procedure was carried out as approved by the Animal Care and Use Committee at Wake Forest University School of Medicine. The presence of antibodies in the rabbit sera was confirmed by Ouchterlony immuno diffusion. All sera showed the presence of precipitating anti-hFIX antibodies.

Results

Enhanced cellular production of functional r-hFIX by siRNA Silencing of Calumenin in BHK Cells Engineered to Overexpress VKORC1 and r-hFIX In a previous paper (11) r-hFIX producing BHK cells were engineered to stably over express various proteins known to belong to the vitamin K-dependent γ-carboxylation system (17). We showed that VKOR is the rate limiting step in this post translational protein modification system (11,14) and found that functional r-hFIX was produced at high levels in cells engineered to stably overexpress VKORC1, the γ-carboxylase cofactor producing enzyme of the vitamin K cycle (11). Here we set out to determine if reducing calumenin function in our engineered BHK cells would improve production of functional r-hFIX. Since the hamster genome is not known, we sequenced the hamster calumenin cDNA and provided DHARMACON with the hamster sequence (gi: 63148518) for siRNA design. We ordered the SMART pool version of the technology which contained 50 nmols of 4 nucleotides with potential for hamster calumenin mRNA silencing. BHK cells stably overexpressing VKORC1 and r-hFIX were transfected with the various concentrations of the siRNA SMART pool shown in FIG. 1. The effect of siRNA silencing on γ-carboxylase and VKOR activities are shown in FIG. 1, A and B respectively. Also shown are Western blots of calumenin present in the different siRNA SMART pool treated cells and silencing of the protein in % of the control (0 nM siRNA). In addition, blotting with an α-Actin antibody is shown which verified equal loading of protein in each lane. As shown in FIG. 1A, γ-carboxylase activity measured as $^{14}CO_2$-γ-carboxylation of the peptide substrate FLEEL increased 3-fold in cell cultures containing 150-200 nM of the siRNA SMART pool. These concentrations of the siRNA SMART pool also had a smaller but significant activating effect on VKOR activity (FIG. 1B).

Figure 2:
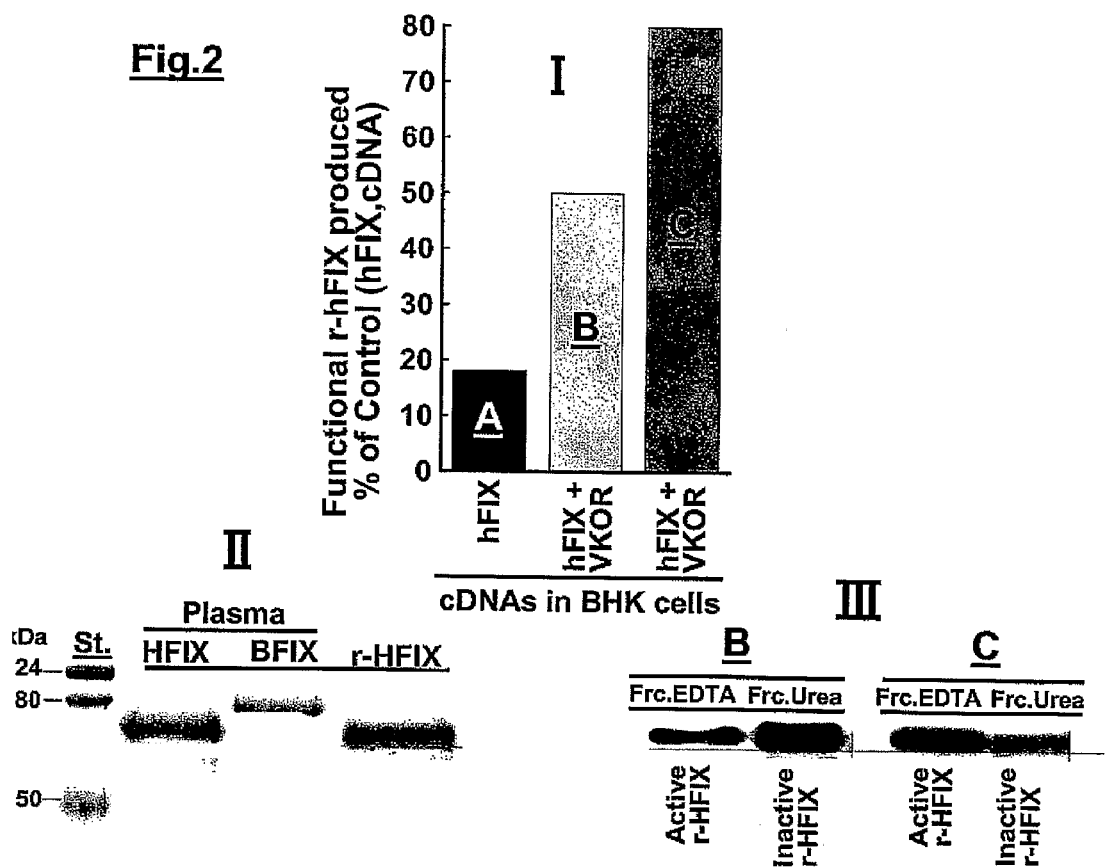
FIG. 2 shows the effect of calumenin siRNA silencing on production of functional r-hFIX by BHK cells engineered to overexpress r-hFIX and VKORC1. Functional and non-functional r-hFIX were purified from cell media obtained from BHK cells engineered to overexpress 1) r-hFIX only (Panel I, A) and 2) r-hFIX+VKORC1 that had not been treated (panel I, B) and treated (panel I, C) with 200 nM of the calumenin siRNA SMART pool (see Experimental Procedures). Panel I shows the production yield of functional r-hFIX obtained from the variously treated BHK cells. Panel II shows Coomassie blue stained factor IX proteins purified from 1) cell medium of BHK cells engineered to overexpress r-hFIX and VKORC1 and treated with 200 nM calumenin siRNA SMART pool (lane, r-HFIX), 2) human plasma factor IX (lane, HFIX) and 3) bovine plasma factor IX (lane, BFIX). Panel III shows Western blots of functional (Frc.EDTA) and non functional (Frc.Urea) r-hFIX purified from medium from BHK cells engineered to overexpress r-hFIX and VKORC1 (III, B) and medium from the same engineered cells treated with 200 nM of the calumenin siRNA SMART pool (III,C). The blots were developed with a factor IX antibody that does not discriminate between active and inactive protein. Each purified protein were Western blotted such that each blot represents the total amount of protein isolated.

To determine if reducing calumenin function increased production of functional r-hFIX, r-hFIX was purified from the medium from (r-hFIX+VKORC1) overexpressing BHK cells that had been treated with 200 nM of the siRNA SMART pool and compared to the yield obtained from cells stably overexpressing (hFIX+VKORC1) but not treated with the SMART pool. Purification of functional and non functional r-hFIX from each medium was carried out by conformational and non-conformational specific immunoaffinity chromatograpy on anti-factor IX immobilized Sepharose as described in detail in a previous article (11). Functional r-hFIX purified from the 200 nM siRNA SMART pool medium had a specific activity of 147 units/mg and SDS-PAGE of the purified protein is shown in FIG. 2, panel II, lane r-HFIX. Factor IX purified from human and bovine plasmas are also shown in panel II, lanes HFIX and BFIX respectively. The stained SDS-PAGE gel showed that purified r-hFIX did not contain bovine FIX which potentially could have been a contaminant from fetal bovine serum used in the early stages of culturing engineered BHK cells for r-hFIX production and purification according to our published protocol (11). FIG. 2, panel III, shows Western blots of functional (lane; Frc. EDTA) and non-functional (lane; Frc.Urea) r-hFIX purified from (r-hFIX+VKORC1) overexpressing BHK cells that had not been treated (B) and treated (C) with 200 nM of the siRNA SMART pool. The intensity of the Western blots shown in each lane is representative for the total isolated amount of protein present in the various fractions of purified r-hFIX (see Experimental Procedures). As can be gleaned from FIG. 2, panel III, significantly more functional r-hFIX (Frc.EDTA) was produced by the (r-hFIX+VKORC1) overexpressing and SMART pool treated BHK cells (C) than from the (r-hFIX+VKORC1) overexpressing BHK cells where calumenin had not been silenced with the SMARTpool (B). Functional r-hFIX produced in % of total r-hFIX produced by; 1) r-hFIX overexpressing (A), 2) (r-hFIX+VKORC1) overexpressing (B) and 3) (r-hFIX+VKORC1) overexpressing and SMART pool treated (C) BHK cells is shown in FIG. 2, panel I. For (A), (B) and (C) shown as bar graphs in panel I, the yields were 18%, 50% and 80% respectively. We conclude from these data that silencing of the γ-carboxylase inhibitor calumenin in the (r-hFIX+VKORC1) overexpressing BHK cells significantly increased the cells capacity to γ-carboxylase the pool of recombinant human factor IX appearing in the lumen of the ER.

We have shown previously (11) that overexpression of r-hFIX by BHK cells, following retroviral infection and selection, results in clones of r-hFIX producing cells which produce the same amount of the recombinant protein whether or not the cells also overexpress proteins of the vitamin K-dependent γ-carboxylation system. In this study we found that treating the cells with the siRNA SMART pool also did not affect total synthesis of r-hFIX (data not shown). Synthesis of functional r-hFIX by the (VKORC1+r-hFIX) overexpressing and siRNA SMART pool treated BHK cells were estimated to be 13 µg/day/$10^6$ cells in contrast 3 µg/day/$10^6$ cells by BHK cells stably overexpressing only r-hFIX.

Figure 3:
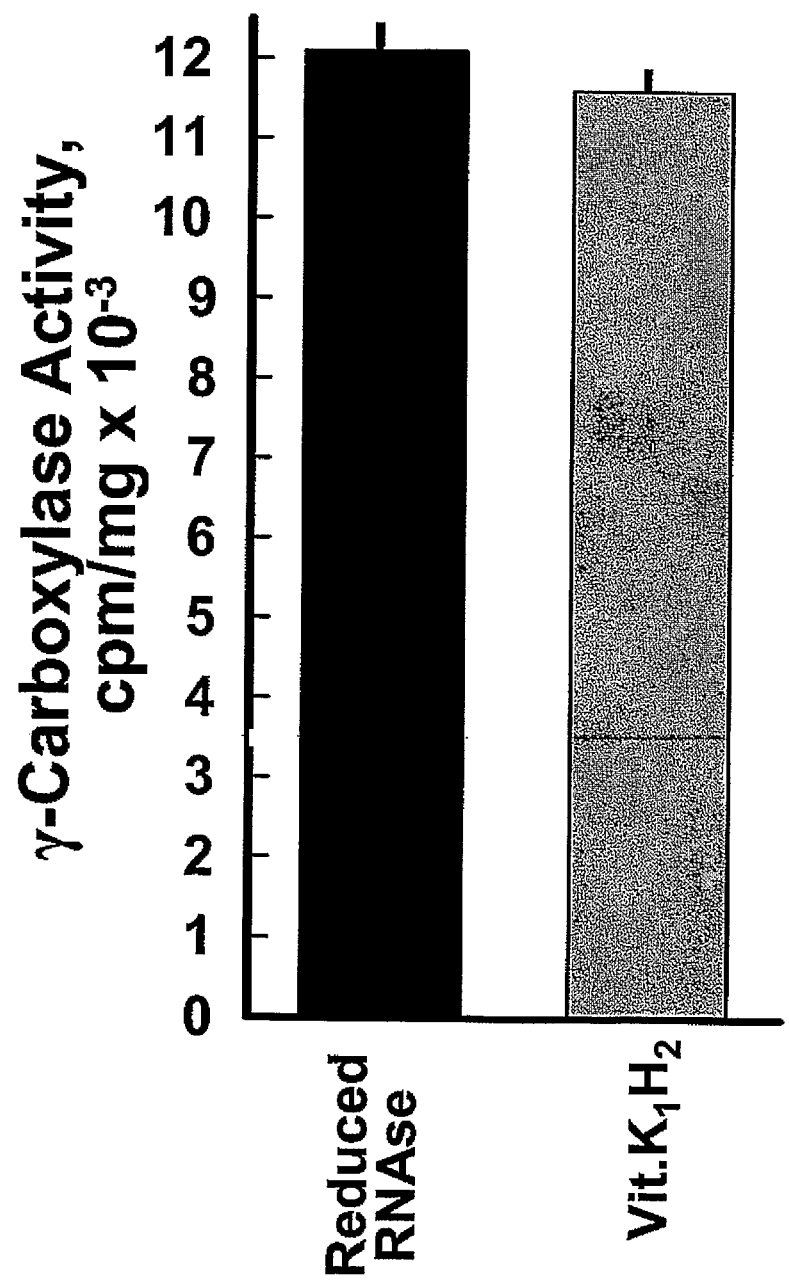
FIG. 3 shows gamma-carboxylase activity triggered by reduced bovine RNAse. Rat liver microsomes extracted of luminal and peripherally bound membrane proteins (see Experimental Procedures) were tested for FLEEL γ-carboxylation when the reaction was triggered by reduced RNAse (black bar) and reduced vitamin $K_1H_2$ (shaded bar). When reduced RNAse was used, the test system contained 40 µM vitamin $K_1$ 2,3-epoxide as the source of the γ-carboxylase cofactor. No DTT was present in the assays. Each bar represents the average activity of three parallel incubations. Standard deviation is shown on each bar.
Figure 4:
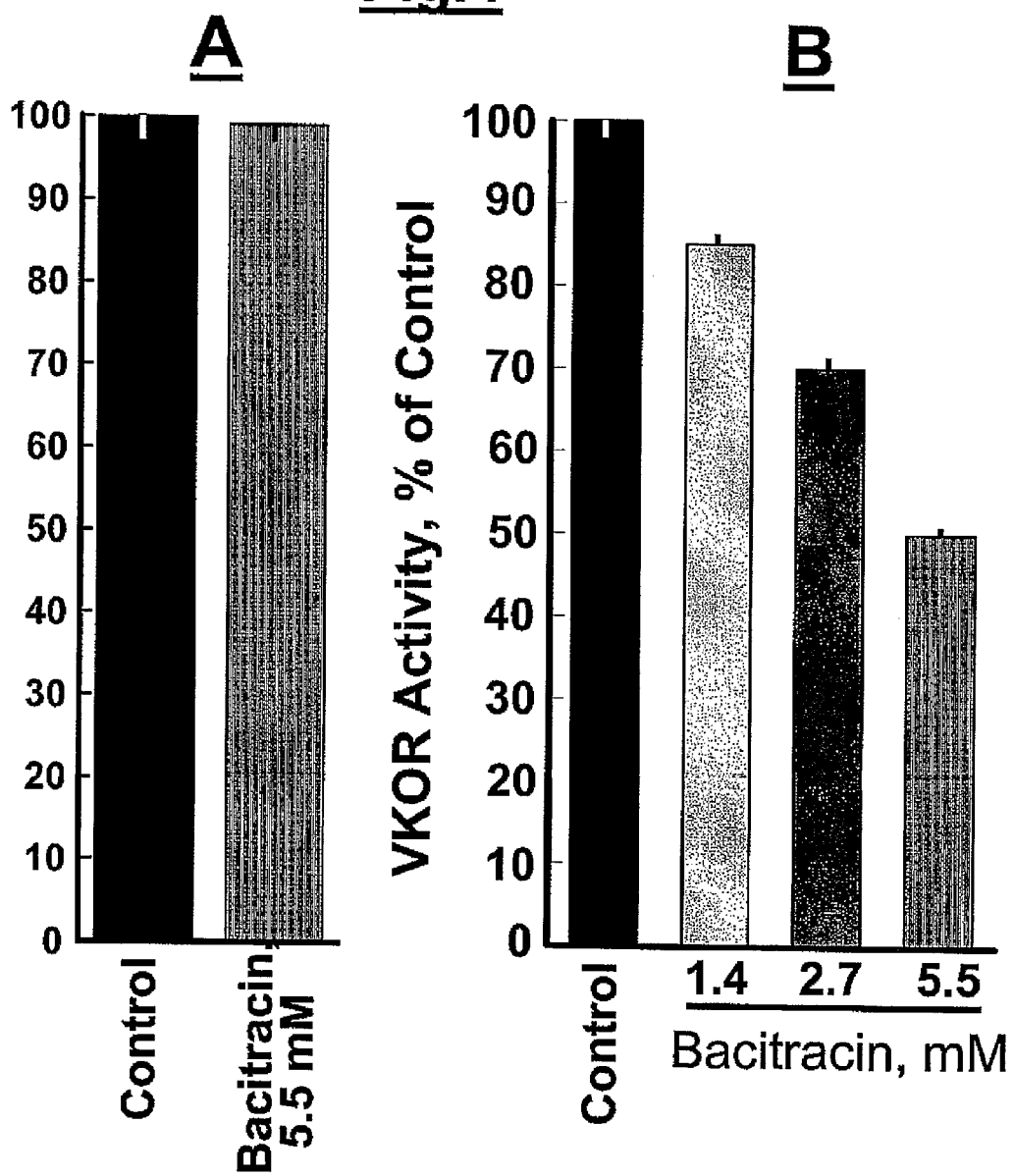
FIG. 4 shows bacitracin inhibition of reduced RNAse triggered VKOR activity. Extracted rat liver microsomes (see legend to FIG. 3) were tested for VKOR activity triggered with 0.32 mM reduced RNAse (panel B) and 5 mM DTT (panel A) present in the assay system. VKOR activities are presented as % of controls which contained no PDI inhibitor. The controls with DTT and reduced RNAse had 87% and 67% conversion of the epoxide to vitamin K1 respectively. Panel B shows reduced RNAse triggered VKOR activity in the presence of various concentrations of bacitracin. Panel A shows that bacitracin has no effect on DTT triggered VKOR activity. Each bar is the average activity of three parallel incubations and standard deviations are indicated as lines on top of the bars.
Figure 5:
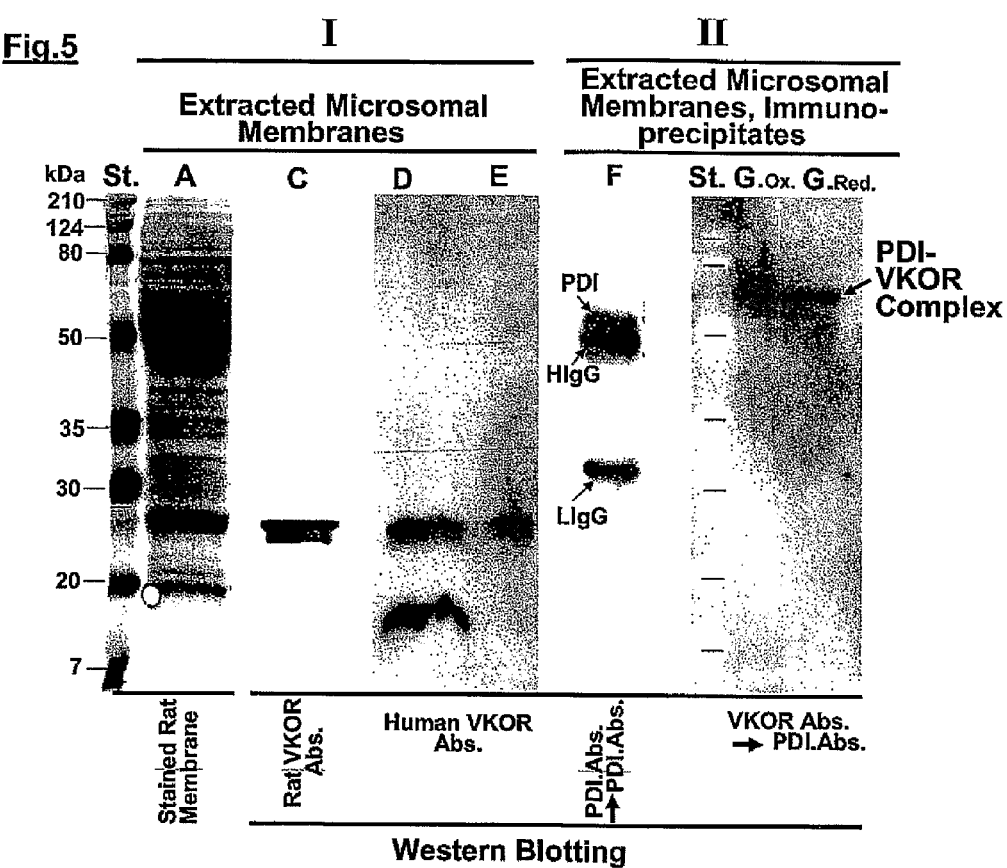
FIG. 5 shows biochemical identification of the PDI-VKORC1 enzyme complex. Extracted rat and human liver microsomes (see legend to FIG. 3) were solublized in buffer D containing 20 mM NEM per ml. Soluble proteins were transferred into RIPA buffer by gel filtration (see Experimental Procedures). Lane A, in Panel I, shows Coomassie blue stained proteins present in extracted rat liver microsomal membranes. Lane St. has standard proteins. Lane C shows a Western blot of the proteins in lane A with rat VKORC1 peptide antibodies. Lanes D and E show Western blots of extracted human and rat liver microsomes respectively with peptide antibodies raised against an epitope on human VKORC1 (see Experimental Procedures). Panel II, lane F shows a Western blot of an immunoprecipitate of the solubilized rat proteins isolated with monoclonal (mouse) PDI antibodies and developed with the same antibody as the first antibody and horse radish conjugated goat anti-mouse antibody as the second antibody. The sequence of precipitating and first antibody is shown. Rat PDI and the heavy (HIgG) and light (LIgG) chains of mouse IgG are visible. Panel II, lanes G.Ox. and G.Red show immunoprecipitates obtained with rat VKORC1 antibodies and their Western blots developed with the mouse PDI monoclonal antibody as the first antibody and horse radish conjugated goat anti-mouse IgG as the second antibody. The sequence of precipitating and first antibody is shown. Preparation of the samples before SDS-PAGE in 8-12% CRITERION gels is described in detail in Experimental Procedures. The samples in G.Ox and G.Red were not reduced and reduced with ME respectively prior to electrophoresis.

PDI Forms a Complex with VKORC1 and Participates in γ-Carboxylation:

The in vivo electron donor for vitamin K1 2,3-epoxide reduction by VKOR of the vitamin K cycle has never been identified although a variety of candidate donors have been suggested including lipoamide (22), and thioredoxin (23). Based on experiments with crude rat liver microsomes, Soute et al. (15) found that reduced RNAse could "drive" γ-carboxylation of FLEEL and proposed that PDI, via oxidative refolding of newly synthesized proteins translocated into the ER, could be the ultimate source of energy and electrons needed for vitamin $K_1$ 2,3-epoxide reduction. However their model which included thioredoxin as an intermediate electron carrier between PDI and VKOR lost some attention when Preusch (24) showed that immunodepletion of thioredoxin from a microsomal in vitro system did not affect VKOR activity. We found the refolding hypothesis by thiol oxidation to be an attractive hypothesis and focused on PDI as a microsomal protein involved in transfer of electrons to the thioredoxin-like CXXC center in VKORC1. PDI is an abundant protein in the ER with a concentration that exceeds >2% of the total soluble proteins normally found in the lumen of liver microsomes (25). As described in a previous paper (17) we use a modified version of the conventional carbonate, pH 11.5 procedure to prepare microsomal membrane vesicles devoid of luminal as well as proteins bound peripherially to the ER membrane. These extracted vesicles are shown to harbor all protein components needed for operation of the vitamin K-dependent γ-carboxylation system and the system has high activity due to removal of the inhibitor calumenin by extraction (17). Thus we could prepare a highly active γ-carboxylation test system with a significantly reduced concentration of PDI. As shown in FIG. 3 we found that when reduced RNAse (black bar) was added to this test system, oxidative folding of RNAse could "drive" vitamin $K_1$ 2,3-epoxide reduction by the vitamin K cycle to produce reduced vitamin $K_1H_2$ cofactor for γ-carboxylase. Indeed, reduced RNAse triggered FLEEL γ-carboxylation to the same extent as chemically reduced vitamin $K_1H_2$ (shaded bar). This finding suggested that oxidative folding of RNAse was carried out by PDI present in the extracted microsomal membranes and that reoxidation of the CGHC center in the a' domain of PDI (25) was either directly or indirectly responsible for reduction of the CXXC center in VKORC1. To provide more convincing data that PDI was involved, we included the PDI inhibitor bacitracin (26, 27) in our experiments. As shown in FIG. 4B there was a dose dependent inhibition of VKOR activity by bacitracin. RNAse with scrambled disulfide bounds, a competitive inhibitor of RNAse oxidative folding by PDI (28), was found also to inhibit VKOR activity (data not shown). On the other hand bacitracin had no effect on VKOR activity when vitamin $K_1$ 2,3-epoxide reduction was triggered with DTT (FIG. 4A) which confirmed earlier data showing that DTT directly can reduce the CXXC center in VKOR (14). Since reduced glutathione (29) and thioredoxin (24) had been eliminated as candidate reductants of the CXXC center in VKORC1, we set out to identify a putative red/ox intermediate complex formed between PDI and VKORC1. To prevent rapid disruption of the S-S linked intermediate we blocked free thiols with NEM. Blocking of the C-terminal Cys residue in the CXXC center has been shown to be important for preservation of such red/ox intermediates (30). FIG. 5 is a composite of several experiments and presents evidence for the existence of a PDI-VKORC1 complex. The figure has two panels labeled; I) Extracted Microsomal Membranes and II) Extracted Microsomal Membranes, Immunoprecipitates. Panel I, lane A shows Coomassie blue stained proteins present in the extracted microsomal membranes used for the experiments when separated by SDS-PAGE. St. is stained standard proteins. Lane C is a Western blot of the proteins seen in lane A with the anti-rat VKORC1 peptide antibodies prepared by our laboratory and described in (17). Lanes D and E are Western blots of extracted human and rat liver microsomes respectively with an anti-VKORC1 peptide antibody made against a peptide from human VKORC1 (see Experimental Procedures). Lane D shows two forms of VKORC1 with different molecular masses in humans while lane E shows that the rat has the form with the higher molecular mass and is recognized by the human peptide antibodies. The rat peptide antibodies prepared by our laboratory did not recognize human VKORC1 (not shown). These blotting images convincingly demonstrated that the affinity purified anti-VKORC1 peptide antibodies recognize VKORC1 in the extracted microsomal membranes. Panel II, lane F shows a Western blot of an immunoprecipitate of PDI isolated with a PDI monoclonal antibody and developed with the same PDI antibody as the first antibody followed by horseradish peroxidase conjugated goat anti-mouse IgG as the second antibody. Thus in addition to the 55 kDa PDI protein, the heavy (HIgG) and light (LIgG) chains of the PDI mouse monoclonal antibody are seen. This precipitation experiment was done to demonstrate that PDI was present in the extracted microsomal membrane vesicles and that PDI could be immunoprecipitated from a solution of the extracted vesicles. Panel II, lanes G.Ox and G.Red show Western blots of immunoprecipitates obtained with the rat VKORC1 antibodies PDI mouse and developed with the PDI antibodies as the first antibody and visualized with horseradish peroxidase conjugated goat anti-mouse IgG as the second antibody. The individual samples loaded in lanes G.Ox and G.Red were not reduced and reduced with ME respectively prior to SDS-PAGE. Both lanes demonstrate the existence of a PDI-VKORC1 complex with an anticipated higher molecular weight than PDI. Importantly, the complex did not dissociate when reduced with ME prior to SDS-PAGE (lane G.Red.). Furthermore the PDI-VKORC1 complex was also seen whether or not free thiols had been blocked with NEM prior to electrophoresis. This suggests that VKORC1 and PDI are tightly associated in the ER membrane. We have also demonstrated the existence of the PDI-VKORC1 complex in HEK293 cells transfected with a c-myc-tagged VKORC1 construct. In this experiment c-myc antibodies were used to immunoprecipitate the complex from a RIPA buffer extract of the cells and the complex was identified with the PDI antibodies (see Experimental Procedures; gel image not shown).

Discussion

The data presented herein demonstrate that calumenin is an inhibitor of the vitamin K-dependent γ-carboxylation system. These findings made us focus on siRNA silencing of calumenin in our BHK cells engineered to overexpress r-hFIX and components of the vitamin K-dependent γ-carboxylation system as a potential additional strategy to increase production of fully γ-carboxylated, functional r-hFIX. We demonstrate herein that this strategy was successful. BHK cells stably overexpressing VKORC1 and r-hFIX, when treated with 150-200 nM of the calumenin siRNA SMART pool, produced 80% of the r-hFIX as a functional coagulation factor as opposed to 18% produced by BHK cells relying on their endogenous vitamin K-dependent γ-carboxylation system for production. This translated into a cellular production of 13 μg/day/$10^6$ cells by the (VKORC1+r-hFIX) overexpressing and calumenin silenced BHK cells as opposed to 3 μg/day/$10^6$ cells of the BHK cells overexpressing only r-hFIX. In accordance with the present invention, a eukaryotic cell system with high capacity for post translational vitamin K-dependent γ-carboxylation of proteins has been created. This high capacity system relies on 1) overexpression of VKORC1, a subunit of the γ-carboxylase cofactor producing VKOR enzyme complex which is the rate limiting step in the system and 2) down regulation of the γ-carboxylation inhibitor calumenin. As demonstrated and discussed in a previous article (11), overexpression of γ-carboxylase inhibits production of functional r-hFIX by an unknown mechanism. However, because the endogenous γ-carboxylase has a high γ-carboxylation capacity, it can fully γ-carboxylate a large fraction of r-hFIX present in the ER if enough cofactor is available. The engineered BHK cell system does not restrict itself to production of r-hFIX. Theoretically, all proteins of the vitamin K-dependent protein family (1) could be overexpressed and highly produced as functional proteins by this cell system.

Calumenin is a member of the Ca++ binding CREC family of chaperone proteins found in the ER (31). Northern blot analyses have demonstrated high expression of calumenin in extrahepatic tissues which also exhibit low γ-carboxylation activity when compared to the liver (32).

The present study provides for the first time evidence that PDI, a thioredoxin like oxidoreductase and chaperone present at high concentration in the ER, associates with VKORC1 to form the warfarin sensitive VKOR enzyme complex capable of reducing vitamin K1 2,3-epoxide to vitamin K1H2 (2). We (17) and Rost et al. (34) have shown by mutagenesis of the Cys residues in the thioredoxin like CXXC center in VKORC1 that the center is needed for electron transfer to vitamin K1 2,3-epoxide. VKORC1 also appears to harbor the vitamin K1 2,3-epoxide binding site in a location distant from the CXXC center (34). In the past several investigations have provided data which suggest that the anticoagulant warfarin exerts its pharmacological effect by preventing red/ox cycling of the CXXC center in VKORC1 by binding to the center (2). Recent data by Rost et al. (34) further support this notion by identifying a Tyr residue close to the CXXC center which, when mutated, affects warfarin sensitivity of VKOR.

The finding that reduced RNAse can support γ-carboxylation and "drive" vitamin K1 2,3-epoxide reduction by the vitamin K cycle is consistent with the notion that PDI acts as the reductase for the CXXC center in VKORC1. Initially we expected PDI to form a VKORC1-S-S-PDI intermediate red/ox complex which, when stabilized by NEM labeling of the C-terminal Cys residue in the center, would dissociate upon reduction with ME prior to SDS-PAGE (30). On the contrary, we found the complex to be stable in SDS-PAGE both with and without disulfide reduction by ME. This suggests that part of the PDI protein pool in the ER forms a stable complex with the integral membrane protein VKORC1 (17). The complex remained intact in the extracted microsomes we prepared from rat liver microsomes.

PDI is organized into five domains (a, b, b', a' and c) where the a and a' domains are homologous to thioredoxin and contain CGHC red/ox centers which mediate some of the PDI's activities including isomerase and oxido/reductase (25). It appears that the b' domain primarily acts as the binding site for PDI substrates and that binding involves hydrophobic interactions (35). This would fit well with the hydrophobic environment around the CXXC center in VKORC1 (17) and potentially puts an unblocked thioredoxin a' domain in close proximity to the CXXC center in VKORC1. Indeed it is well established that binding of PDI to other proteins does not necessarily involve its thiol red/ox centers (28), as oxidation of the reduced CGHC centers are carried out by the ER oxidase ERO1 (25).

Figure 6:
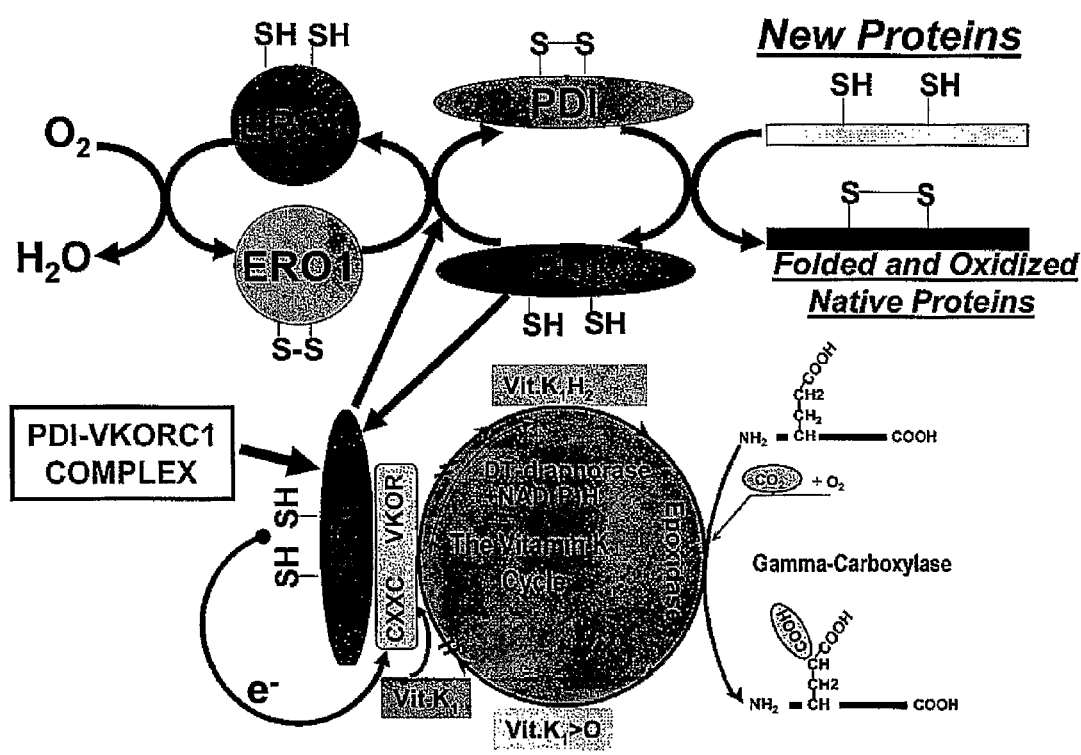
FIG. 6 shows that oxidative protein folding in the ER is linked to post translational γ-carboxylation of proteins. A hypothetical model of this process is shown. The ER localized chaperone, red/ox and isomerase protein PDI acquires reduced thioredoxin related CGHC centers in its effort to enforce correct oxidative folding of disulfide containing newly synthesized proteins. Reoxidation of reduced PDI by endoplasmic reticulum oxidase1 (ERO1) is a major pathway for the continuos operation of PDI in oxidative folding. However our data suggest that some of the PDI proteins in the ER form stable complexes with the integral VKORC1 protein in the ER membrane. We propose that the PDI-VKORC1 protein complex is responsible for warfarin sensitive reduction of vitamin K1 2,3-epoxide to reduced vitamin K1H2, the essential cofactor for γ-carboxylase Gla modification of proteins.

PDI is known to be a subunit of other proteins including prolylhydroxylase (36), triglyderide transferase (37) and more recently NAD(P)H oxidase in vascular smooth muscle cells (28). Based on this knowledge and our finding of a complex between VKORC1 and PDI we propose that operation of the vitamin K cycle and post translational γ-carboxylation of proteins is linked to protein synthesis and oxidative fording of proteins in the ER. In the schematic drawing shown in FIG. 6, we propose that New Proteins become oxidatively folded by PDI which subsequently acquires reduced CGHC centers. A known pathway for PDI thiol reoxidation in the ER is oxidation by the ER oxidase ERO1 which ultimately leads to formation of $H_2O$ (25,38). Our data support the notion that part of the reduced PDI protein pool becomes associated with VKORC1 in the ER membrane. We hypothesize that the reduced CGHC center in PDI "feeds" electrons into the CXXC center in VKORC1 for vitamin K1 2,3-epoxide reduction.

Example 3

Increased Production of Factor VII

Figure 10:
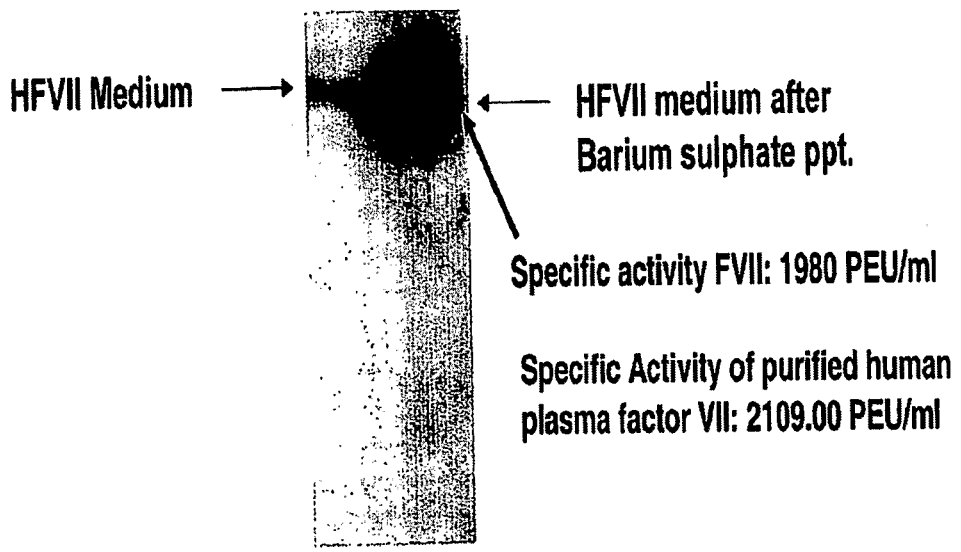
FIG. 10 is a Western Blot of recombinant Factor VII. See Example 3 for details.

Cell lines that stably overexpress recombinant human factor VII and VKORC1 are currently being developed. A cDNA vector comprising human factor VII cDNA was purchased from Biochain. The complete factor VII cDNA encoding the protein was amplified via PCR and cloned into a pBUDCE4.1 dual vector (Invitrogen). The cDNA PCR product was sequenced on both strands and confirmed to have no sequencing errors. We transfected BHK cells with the factor VII vector and isolated recombinant factor VII protein which was secreted into the medium. We used BaCitrate to absorb gamma-carboxylated factor VII from the medium. Shown in FIG. 10 is a Western blot of recombinant factor VII in the medium and after its absorption onto BaCitrate, which is the conventional method used to absorb fully gamma-caroxylated, active vitamin K-dependent proteins from plasma and cell media. The specific activity of the BaCitrate absorbed protein had specific activity that was close to purified plasma factor VII. Thus we have generated a vector which produces high levels of Factor VII with demonstrable specific activity in BHK cells.

To determine if siRNA silencing of calumenin in BHK cells stably transfected with VKORC1 and human FVII would increase the yield of functional recombinant factor FVII the following experiment was performed. A cell line was created by co-transfecting BHK cells with a mixture of pBUDCE4.1 vectors containing the VKORC1 cDNA and the human factor VII cDNA respectively. Stable cell lines were tested for increase in VKOR activity and factor VII production and one selected line among these was used for the experiments. Control cells were transient transfected with 100 μM of scrambled siRNA and test cells transfected with 100 μM of the SMART POOL siRNA made against hamster calumenin which we had used before to silence calumenin in BHK cells making r-hFIX. The control and the SMART pool cell lines were incubated for 48 hours and the medium harvested for collecting secreted factor VII.

The medium was diluted 8:1 with 2.83% barium citrate and 2.4 ml of 1 M $BaCl_2$ was added to 30 ml of the citrate containing medium. The Ba citrate salt was allowed to form by rotation in a large tube for 30 min and the salt collected by centrifugation at 4° C. at 2000×g. The salt was dissolved in 100 ml saline which subsequently was made 200 mM with new Ba citrate and 200 $BaCl_2$ to form a new salt precipitate for absorption of gamma-carboxylated factor VII. The salt was collected by centrifugation and resuspended in a small volume of 0.5 M EDTA, pH 7.6. The suspension was dialyzed against 0.5 M EDTA pH 7.6 until all salt and absorbed proteins were in solution. The solution was dialyzed extensively against Tris-buffered saline containing 5 mM benzamidine and concentrated on an Amicon Ultrafiltration Polyethersulfone Membrane (5,000 cut of) (Millipore). By measuring factor VII protein in the Ba-citrate absorbed protein fractions from control cells and calumenin SMART POOL siRNA treated cells we found 2.2-fold more factor VII in the fraction from the SMART POOL siRNA treated cells.

Since Ba-citrate absorption will bind fully gamma-carboxylated factor VII and not factor VII that has not been gamma-carboxylated, we conclude that silencing of calumenin enhances gamma-carboxylation of recombinant factor VII as we previously described for recombinant factor IX.

We also tested gamma-carboxylase activity in the control cells and the cells that were treated with the calumenin SMART POOL siRNA. The activity in control cells and in SMART POOL siRNA treated cells were 37,000 cpm/mg and 62,000 cpm/mg respectively. This control experiment shows that the siRNA SMART POOL had enhanced the gamma-carboxylation system in BHK cells needed for gamma-carboxylation of recombinant factor VII.

We have decided to include HEK 293 cells in our continued efforts to create "super cells" overexpressing the coagulation factors described herein. Suitable cells for this purpose will overexpress VKORC1 and underexpress the γ-carboxylase inhibitor calumenin, (e.g., the cells will contain siRNA which silences calumenin expression.

In connection with all of these efforts, the following recombinant cell lines have been or will be produced.
BHK Cells:
  1. VKORC1+ human Factor IX (retro virally introduced)+ hair pin shRNA Vector (5584 bp) with HuSH shRNA against human calumenin (CALU). Selective markers: VKORC1, zeocin; Retroviral introduced Factor IX, G418; shRNA, puromycin.

2. VKORC1+human Factor VII (retro virally introduced)+ hair pin shRNA Vector (5584 bp) With Hu SH shRNA against human calumenin (CALU). Selective markers: VKORC1, zeocin; Retroviral introduced Factor VII, G418; shRNA, puromycin.

HEK293 Cells:
1. VKORC1+human Factor IX (retro virally introduced)+ hair pin shRNA Vector (5584 bp) with HushRNA against human calumenin (CALU). Selective markers: VKORC1, zeocin; Retro virally introduced Factor IX, G418; shRNA, puromycin.
2. VKORC1+human Factor VII (retro virally introduced)+ hair pin shRNA Vector (5584 bp) with HuSH shRNA against human calumenin (CALU). Selective markers: VKORC1, zeocin; Retro virally introduced Factor VII, G418; shRNA, puromycin.

The HuSH 29mer Constructs against human Calu RNA have been purchased from ORIGENE as one product of their supply of siRNAs made against all genes of the human genome (catalog #TR314215).

Figure 11:
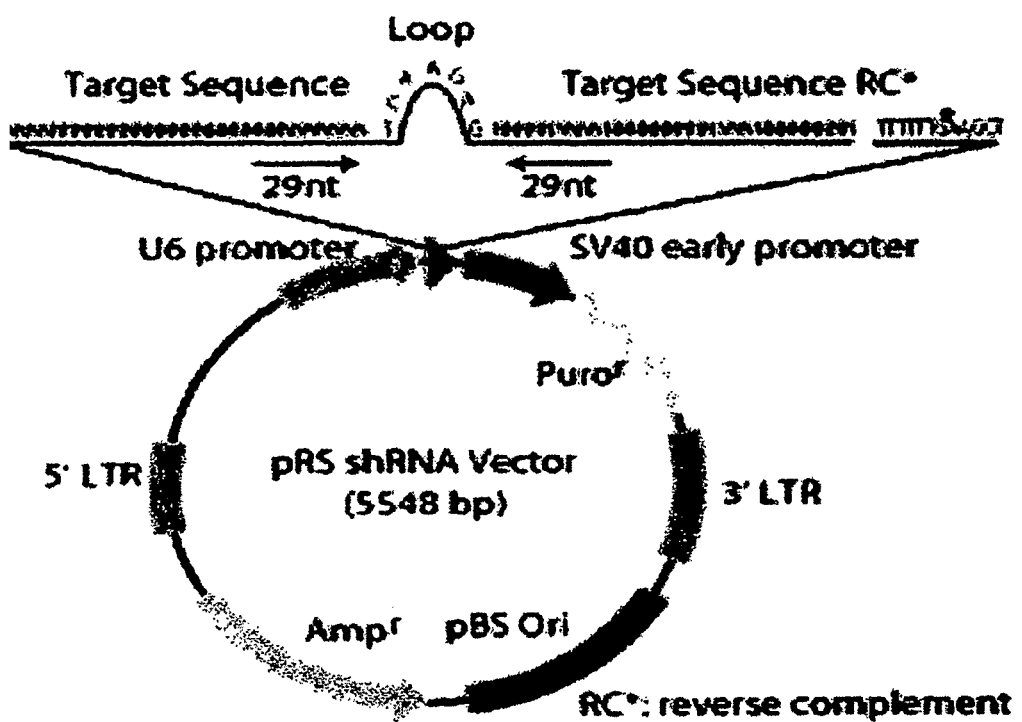
FIG. 11 is a schematic diagram of the pRS shRNA vector.

The 4 nucleotides listed below have been put into the pRSshRNA Vector with puromycin resistance. See description above and FIG. 11.

|  |  |
|---|---|
| T1356853 | AAGCCTGAGATCAATAAGAAATGTTCAGG (SEQ ID NO: 13) |
| T1356854 | GACAAGGATGGAGACCTCATTGCCACCAA (SEQ ID NO: 14) |
| T1356855 | TGGACCTGCGACAGTTTCTTATGTGCCTG (SEQ ID NO: 15) |
| Ta356856 | CACCAGAAGAGAGCAAGGAAAGGCTTGGA (SEQ ID NO: 16) |

The cells will be transfected with the various constructs listed in points 1 and 2 above, selected for antibiotic resistance and single cell colonies selected and expanded for. This should result in the production of homogenous cell lines which overexpress the clotting factors described herein. Many different transfection protocols are available to the skilled artisan and do not need to be listed here. See for Example Current Protocols in Molecular Biology, Ausbel et al. eds., J. W. Wiley and Sons.

In summary, the present methods and cell lines provide the pharmaceutical industry with the means to significantly reduce the production costs associated with the synthesis of recombinant vitamin K-dependent proteins which include, without limitation, Factors IX and VII.

References

1. Furie, B. and Furie, B. C. (1992) *NEJM* 326: 800-806
2. Wallin, R., and Hutson, S. M. (2004) *Trends Mol Med* 10: 299-302
3. Suttie, J. W. (1978) *Handbook of Lipid Research* (De-luca, H F., ed), pp. 211-277, Plenum Press, New York
4. Furie, B., and Furie, C. (1988) *Cell* 53, 505-518
5. Forastiero, R. R., Martinuzzo, M. E., Lu, J., and Broze, J. *J Thromb. Haemostas* 1: 1764-1770
6. Hedner, U. (2001) *Semin Hematol* 38(4 Suppl 12): 43-47.
7. Roth, D. A., Kessler, C. M., Pasi, J., Rup, B., Courter, S. G. and Tubridy, K. L. (2001) *Blood* 98: 3600-3606.
8. Berbard, G, R., Vincent, J-L., Laterre, P-F., LaRosa, S. P., Dhainaut, J-F., Lopez-Rodriguez, A., Steingrub, J. S., Garber., G. E., Helterbrand, J. D., Wesley Eli, E. and Fisher, C. J. (2001) *NEJM* 344: 699-709.
9. Kaufman, R. J., Wasley, L. C., Furie, B. C., Furie, B and Shoemaker, C. B. (1986) *J Biol. Chem.* 261: 9622-9628.
10. Rehemtulla, A., Roth, D. A., Wasley, L. C., Kuliopulos, A., Walsh, C. T., Furie, B., Furie, B. C. and Kaufman, R. J. (1993) *Proc. Natl. Acad. Sci. USA* 90: 4611-4615.
11. Wajih, N., Hutson, S. M., Owen, J., and Wallin, R. (2005) *J Biol Chem* 280: 31603-31607
12. Rost. S., Fregin, A., Ivaskevicius, V., Conzelmann, E., Hortnagel. K., Pelz, H. J., Lappegard, K., Seifried, E., Scharrer, I., Tuddenham, E. G., Muller, C. R., Strom, T. M., and Oldenburg, J. (2004) *Nature.* 427: 537-541
13. Goodstadt, L., and Ponting, C. P. (2004) *Trends Biochem Sci* 29: 289-292
14. Wallin, R., Sane. D. C., and Hutson, S. M. (2002) *Thromb Res* 108: 221-226
15. Soute, B. A., Groenen-van, M. M., Holmgren, A., Lundstrom, L., and Vermeer, C. (1992) *Biochem J* 281: 255-259
16. Wajih, N., Sane, D. C., Hutson, S. M., and Wallin. R. (2004) *J Biol Chem* 279: 25276-25283
17. Wajih, N., Sane, D. C., Hutson, S. M. and Wallin, R. J. (2005) *J. Biol Chem.* 280:10540-10547
18. Wallin, R., Hutson, S. M., Cain, D., Sweatt, A., and Sane, D. C. (2001) *FASEB J* 15: 2542-2544
19. Wallin, R., and Martin L. F. (1985) *J Clin Invest* 76: 1879-1884
20. Rupp, K., Birnbach, U., Lundstrom, J., Nguyen, Van P., and Soling, H-D. (1994) *J Biol Chem* 269: 2501-2507
21. Wajih, N., Borras, T., Xue, W., Hutson, S. M., and Wallin. R. (2004) *J Biol Chem* 279: 43052-43060
22. Thijssen, H. H., Janssen, Y. P. Vervoort, L. T. (1994) *Biochem J* 297: 277-280
23. Silverman, R. B., and Nandi, L. N. (1988) *Biochem Biophys Res Commun* 155: 1248-1254
24. Prusch, P. C. (1992) *FEBS Lett* 305: 257-259
25. Wilkinson, B., and Gilbert, H. F. (2004) *Biochim Biophys Acta* 1699: 35-44
26. Mandel, R., Ryser, H. J. P., Ghani, F., Wu., and Peak, D. (1993) *Proc Natl. Acad. Sci USA* 90: 4112-4116
27. Orlandi, P. A. (1997) *J Biol Chem* 272: 4591-4599
28. Janiszewski, M., Lopes, L. R., Carmo, A. O., Pedro, M. A., Brandes, R. P., Santos, C. X. C. and Laurindo, R. M. (2005) *J Biol Chem* 280: 40813-40819
29. Lee, J. J. and Fasco, M. J. (1984) *Biochemistry* 23: 2246-2252
30. Dias-Gunasekara, S., Gubbens, J., Van Lith, M., Dunne, C., Williams, J. A. G., Kataky R., Scoones, D., Lapthorn, A., Bulleid., N., and Benham, A. M. (2005) *J Biol Chem* 280: 33066-33075
31. Honore, B., and Varum, H. (2000) *FEBS Lett* 466: 11-18
32. Yabe, D., Yaniwaki, M., Nakamura, T., Kanazawa, N., Tashiro., and Honjo, T. (1998) *Genomics* 49: 331-333
33. Wallin, R., Wajih, N., Greenwood G, T., and Sane D. C. (2001) *Med Res Rev* 21: 274-301
34. Rost, S., Fregin, A., Hunerberg., M., Bevans, C. G., Muller, C. R., and Oldenburg, J (2005) *Thromb Haemostas* 94: 780-786
35. Koivunen, P., Salo, K. E. H., Myllyharju, J., and Ruddock, L. W. (2005) *J Biol Chem* 280: 5227-5235
36. Pihlajaniemi, T., Helaakoski, T., Tasanen, R., Myllyla, Huhtala., J., and Kivirikko, K. I. (1987) *EMBO J* 6: 643-649
37. Wetterau, J. R., Coms, K. A., Spinner, S. N., and Joiner, B. J. (1990) *J Biol Chem* 265: 9800-9807
38. Benham, A. M., Cabibbo, A., Fassio, A., Bulleid, N., Sitia, R., and Braakman, I. (2000) *EMBO J* 19: 4493-4502
39. Dahlback, B. (2005) *J. Intern. Med.* 257: 209-223.

What is claimed is:

1. A method for production of gamma-carboxylated human Factor IX (hFIX) comprising:

providing a first BHK cell line comprising a nucleic acid encoding hFIX, siRNA molecules directed against calumenin mRNA, and an expression vector encoding VKORC1, said BHK cell line over-expressing VKORC1 relative to BHK cells that lack the expression vector, wherein the level of production of said gamma-carboxylated hFIX exceeds that obtained in a second BHK cell line that is identical to the first except that it lacks said siRNA molecules.

2. The method of claim 1 comprising isolation and optionally purification of said gamma-carboxylated hFIX.

3. A BHK cell line for expressing functional gamma-carboxylated human factor IX (hFIX), the cell line comprising a nucleic acid encoding hFIX, and siRNA molecules directed against calumenin mRNA, an expression vector encoding VKORC1, said BHK cell line over-expressing VKORC1 relative to BHK cells that lack the expression vector.

4. The method of claim 2, comprising treating a blood coagulation disorder in a patient in need thereof by administering to the patient an effective amount of the gamma-carboxylated hFIX.

* * * * *

UNITED STATES PATENT AND TRADEMARK OFFICE
CERTIFICATE OF CORRECTION

PATENT NO.        : 8,647,868 B2                              Page 1 of 1
APPLICATION NO. : 12/095514
DATED             : February 11, 2014
INVENTOR(S)       : Reidar Wallin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1563 days.

Signed and Sealed this

Twenty-ninth Day of September, 2015

Michelle K. Lee
*Director of the United States Patent and Trademark Office*